United States Patent [19]

Leone

[11] 4,276,364
[45] Jun. 30, 1981

[54] ACYLHYDRAZINOPHENYLTHIOUREA NUCLEATING AGENTS AND PHOTOGRAPHIC EMULSIONS AND ELEMENTS CONTAINING SUCH AGENTS

[75] Inventor: Ronald E. Leone, Rochester, N.Y.

[73] Assignee: Eastman Kodak Company, Rochester, N.Y.

[21] Appl. No.: 161,708

[22] Filed: Jun. 23, 1980

Related U.S. Application Data

[63] Continuation-in-part of Ser. No. 122,151, Feb. 19, 1980, abandoned, which is a continuation-in-part of Ser. No. 56,588, Jul. 11, 1979, abandoned.

[51] Int. Cl.$^3$ .................. G03C 1/06; G03C 5/54; G03C 1/40; G03C 1/48
[52] U.S. Cl. ...................... 430/212; 430/217; 430/219; 430/410; 430/598; 430/599; 430/237; 430/604; 430/248; 564/27
[58] Field of Search .............. 430/212, 217, 219, 410, 430/598, 599, 237, 604, 248; 260/552 R

[56] References Cited

U.S. PATENT DOCUMENTS 4,030,925   6/1977   Leone et al. .................. 430/598

*Primary Examiner*—Won H. Louie, Jr.
*Attorney, Agent, or Firm*—Carl O. Thomas

[57] ABSTRACT

Novel 3,3-disubstituted acylhydrazinophenylthiourea nucleating agents are disclosed as well as silver halide photographic emulsions and elements containing silver halide grains capable of forming an internal latent image having the nucleating agents adsorbed to the surface of the silver halide grains. Imaging processes in which these materials participate are also disclosed.

23 Claims, No Drawings

ACYLHYDRAZINOPHENYLTHIOUREA NUCLEATING AGENTS AND PHOTOGRAPHIC EMULSIONS AND ELEMENTS CONTAINING SUCH AGENTS

CROSS-REFERENCE TO RELATED APPLICATION(S)

This is a continuation-in-part of copending patent application Ser. No. 122,151, filed Feb. 19, 1980, which is a continuation-in-part of Ser. No. 056,588, filed July 11, 1979, both now abandoned.

FIELD OF THE INVENTION

The present invention is directed to novel photographic emulsions and elements and to novel adsorbed arylhydrazide nucleating agents. More specifically, this invention is directed to novel adsorbed arylhydrazinophenylthiourea nucleating agents and to photographic emulsions and elements containing such nucleating agents in combination with silver halide grains capable of forming an internal latent image.

BACKGROUND OF THE INVENTION

Photographic elements which produce images having an optical density directly related to the radiation received on exposure are said to be negative-working. A positive photographic image can be formed by producing a negative photographic image and then forming a second photographic image which is a negative of the first negative, that is, a positive image. A direct-positive image is understood in photography to be a positive image that is formed without first forming a negative image. Positive dye images which are not direct-positive images are commonly produced in color photography by reversal processing in which a negative silver image is formed and a complementay positive dye image is then formed in the same photographic element. The term "direct reversal" has been applied to direct-positive photographic elements and processing which produces a positive dye image without forming a negative silver image. Direct-positive photography in general and direct reversal photography in particular are advantageous in providing a more straightforward approach to obtaining positive photographic images.

A conventional approach to forming direct-positive images is to use photographic elements employing internal latent image-forming silver halide grains. After imagewise exposure, the silver halide grains are developed with a surface developer; that is, one which will leave the latent image sites within the silver halide grains substantially unrevealed. Simultaneously, either by uniform light exposure or by the use of a nucleating agent, the silver halide grains are subjected to development conditions that would cause fogging of a negative-working photographic element. The internal latent image-forming silver halide grains which received actinic radiation during imagewise exposure develop under these conditions at a comparatively slow rate, as compared to the internal latent image-forming silver halide grains not imagewise exposed. The result is a direct-positive silver image. In color photography, the oxidized developer that is produced during silver development is used to produce a corresponding positive, direct reversal dye image. Multicolor direct reversal photographic images have been extensively investigated in connection with image-transfer photography.

It has been found advantageous to employ nucleating agents in preference to uniform light exposure in the process described above. The term "nucleating agent" is employed herein to mean a fogging agent capable of permitting the selective development of internal latent image-forming silver halide grains which have not been imagewise exposed in preference to the development of silver halide grains having an internal latent image formed by imagewise exposure.

A favored class of nucleating agents is arylhydrazides. These nucleating agents can be incorporated in a developer solution or directly within a photographic element. Significant advantages have been realized by adsorbing arylhydrazide nucleating agents to the surface of internal latent image-forming silver halide grains. This permits small amounts of the nucleating agents to be employed, as compared with those which are nonadsorbed. However, this narrows the choice of arylhydrazide nucleating agents to those including an adsorption-promoting moiety.

Highly effective adsorbed arylhydrazide nucleating agents are the acylhydrazinophenylthioureas of Leone et al U.S. Pat. No. 4,030,925. These acylhydrazinophenylthioureas are characterized by the 3-position nitrogen atom of the thiourea moiety being mono-substituted.

SUMMARY OF THE INVENTION

This invention has as its purpose to provide novel and highly effective acylhydrazinophenylthiourea nucleating agents. It is a more specific purpose of this invention to provide photographic silver halide emulsions and elements containing these novel arylhydrazinophenylthiourea nucleating agents. The invention provides acylhydrazinophenylthiourea nucleating agents of higher levels of activity. The invention also permits photographic processing over a broader range of pH levels while sustaining nucleating activity.

This invention is directed to 3,3-disubstituted arylhydrazinophenylthiourea nucleating agents, silver halide emulsions containing such nucleating agents and silver halide photographic elements containing at least one silver halide emulsion layer containing such nucleating agents.

In one specific aspect, this invention is directed to a silver halide emulsion comprised of silver halide grains capable of forming an internal latent image and, adsorbed to the surface of the silver halide grains, a nucleating amount of a 3,3-disubstituted acylhydrazinophenylthiourea.

In another aspect, this invention is directed to a photographic element comprised of a support and, coated on the support, a silver halide emulsion layer comprising silver halide grains capable of forming an internal latent image and, adsorbed to the surface of said silver halide grains, a nucleating amount of a 3,3-disubstituted acylhydrazinophenylthiourea.

In still another aspect, this invention is directed to a process of obtaining a direct-positive image comprising imagewise exposing a photographic element according to this invention and selectively developing the silver halide grains remaining unexposed.

Preferred 3,3-disubstituted acylhydrazinophenylthiourea nucleating agents are those of the formula

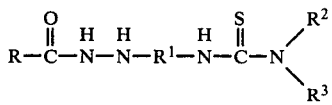

wherein:

R is hydrogen or an alkyl, cycloalkyl, haloalkyl, alkoxyalkyl, or phenylalkyl substituent, $R^1$ is a phenylene or alkyl, halo-, or alkoxysubstituted phenylene group, and $R^2$ and $R^3$ are independently selected from among alkyl, haloalkyl, alkoxyalkyl, or phenylalkyl substituents having from 1 to 18 carbon atoms, a cycloalkyl substituent, a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur, and selenium atoms, the alkyl moieties, except as otherwise noted, in each instance include from 1 to 6 carbon atoms and the cycloalkyl moieties have from 3 to 10 carbon atoms.

More specifically preferred 3,3-disubstituted acylhydrazinophenylthiourea nucleating agents are those of the formula:

wherein

R is hydrogen or methyl and $R^2$ and $R^3$ are independently selected from among alkyl and phenylalkyl substituents, wherein the alkyl moieties are in each instance from 1 to 6 carbon atoms, and a phenyl nucleus having a Hammett sigma value-derived electron-withdrawing characteristic less positive than +0.50, or $R^2$ and $R^3$ together form a saturated heterocyclic nucleus forming a 5- or 6-membered ring, wherein the ring atoms are chosen from the class consisting of nitrogen, carbon, oxygen, sulfur and selenium atoms.

DESCRIPTION OF THE PREFERRED EMBODIMENTS

As indicated by R in formula (I), preferred 3,3-disubstituted arylhydrazinophenylthioureas employed in the practice of this invention contain an acyl group which is the residue of a carboxylic acid, such as one of the acyclic carboxylic acids, including formic acid, acetic acid, propionic acid, butyric acid, higher homologues of these acids having up to about 7 carbon atoms, and halogen, alkoxy, phenyl and equivalent substituted derivatives thereof. In a preferred form, the acyl group is formed by an unsubstituted acyclic aliphatic carboxylic acid having from 1 to 5 carbon atoms. From formula (II), it is apparent that specifically preferred acyl groups are formyl and acetyl. As between compounds which differ solely in terms of having a formyl or an acetyl group, the compound containing the formyl group exhibits higher nucleating agent activity. The alkyl moieties in the substituents to the carboxylic acids are contemplated to have from 1 to 6 carbon atoms, preferably from 1 to 4 carbon atoms.

In addition to the acyclic aliphatic carboxylic acids, it is recognized that the carboxylic acid can be chosen so that R is a cyclic aliphatic group having from about 3 to 10 carbon atoms, such as, cyclopropyl, cyclobutyl, cyclopentyl, cyclohexyl, methylcyclohexyl, cyclooctyl, cyclodecyl, and bridged ring variations, such as, bornyl and isobornyl groups. Cyclohexyl is a specifically preferred cycloalkyl substituent. The use of alkoxy, cyano, halogen, and equivalent substituted cycloalkyl substituents is contemplated.

As indicated by $R^1$ in formula (I), preferred 3,3-disubstituted arylhydrazinophenylthioureas employed in the practice of this invention contain a phenylene or substituted phenylene group. Specifically preferred phenylene groups are m- and p-phenylene groups. Exemplary of preferred phenylene substituents are alkoxy substituents having from 1 to 6 carbon atoms, alkyl substituents having from 1 to 6 carbon atoms, fluoro-, chloro,- bromo- and iodo-substituents. Unsubstituted p-phenylene groups are specifically preferred. Specifically preferred alkyl moieties are those which have from 1 to 4 carbon atoms. While phenylene and substituted phenylene groups are preferred linking groups, other functionally equivalent divalent aryl groups, such as naphthalene groups, can be employed.

Referring again to formula (I), it is apparent that $R^2$ and $R^3$ can independently take a variety of forms. One specifically contemplated form can be an alkyl group or a substituted alkyl group, such as a haloalkyl group, alkoxyalkyl group, phenylalkyl group, or equivalent group, having a total of up to 18, preferably up to 12, carbon atoms. Specifically $R^2$ and/or $R^3$ can take the form of methyl, ethyl, propyl, butyl, pentyl, hexyl, heptyl, octyl, nonyl, decyl or higher homologue group having up to 18 total carbon atoms; a fluoro-, chloro-, bromo- or iodo-substituted derivative thereof; a methoxy, ethoxy, propoxy, butoxy or higher homologue alkoxy-substituted derivative thereof, wherein the total number of carbon atoms are necessarily at least 2 up to 18; and a phenyl-substituted derivative thereof, wherein the total number of carbon atoms is necessarily at least 7, as in the case of benzyl, up to about 18. In a specific preferred form indicated in formula (II) $R^2$ and/or $R^3$ can take the form of an alkyl or phenylalkyl substituent, wherein the alkyl moieties are in each instance from 1 to 6 carbon atoms.

In addition to the acyclic aliphatic and aromatic forms discussed above, it is also contemplated that $R^2$ and/or $R^3$ can take the form of a cyclic aliphatic substituent, such as a cycloalkyl substituent having from 3 to 10 carbon atoms. The use of cyclopropyl, cyclobutyl, cyclopentyl, cyclohexyl, methylcyclohexyl, cyclooctyl, cyclodecyl and bridged ring variations, such as, bornyl and isobornyl groups, is contemplated. Cyclohexyl is a preferred cycloalkyl substituent. The use of alkoxy, cyano, halogen and equivalent substituted cycloalkyl substituents is contemplated.

$R^2$ and/or $R^3$ can also be an aromatic substituent, such as, phenyl or naphthyl (i.e., 1-naphthyl or 2-naphthyl) or an equivalent aromatic group, e.g., 1-, 2- or 9-anthryl, etc. As indicated in both formula (I) and formula (II) $R^2$ and/or $R^3$ can take the form of a phenyl nucleus which is either electron-donating or electron-withdrawing, however phenyl nuclei which are highly electron-withdrawing may produce inferior nucleating agents.

The electron-withdrawing or electron-donating characteristic of a specific phenyl nucleus can be assessed by reference to Hammett sigma values. The phenyl nucleus can be assigned a Hammett sigma value-derived electron-withdrawing characteristic which is the algebraic sum of the Hammett sigma values of its substituents (i.e., those of the substituents, if any, to the phenyl group). For example, the Hammett sigma values of any substituents to the phenyl ring of the phenyl nucleus can be determined algebraically simply by determining from the literature the known Hammett sigma values for each substituent and obtaining the algebraic sum thereof. Electron-withdrawing substituents are assigned positive sigma values, while electron-donating substituents are assigned negative sigma values.

Exemplary meta- and para-sigma values and procedures for their determination are set forth by J. Hine in *Physical Organic Chemistry*, second edition, page 87, published in 1962, H. VanBekkum, P. E. Verkade and B. M. Wepster in *Rec. Trav. Chim.*, Volume 78, page 815, published in 1959, P. R. Wells in *Chem. Revs.*, Volume 63, page 171, published in 1963, by H. H. Jaffe in *Chem. Revs.*, Volume 53, page 191, published in 1953, by M. J. S. Dewar and P. J. Grisdale in *J. Amer. Chem. Soc.*, Volume 84, page 3548, published in 1962, and by Barlin and Perrin in *Quart. Revs.*, Volume 20, page 75 et seq, published in 1966. For the purposes of this invention, ortho-substituents to the phenyl ring can be assigned to the published para-sigma values.

It is preferred that $R^2$ and/or $R^3$ be a phenyl nucleus having a Hammett sigma value-derived electron-withdrawing characteristic less positive than +0.50. It is specifically contemplated that $R^2$ and/or $R^3$ be chosen from among phenyl nuclei having cyano, fluoro-, chloro-, bromo-, iodo-, alkyl groups having from 1 to 6 carbon atoms and alkoxy groups having from 1 to 6 carbon atoms and alkoxy groups having from 1 to 6 carbon atoms, as phenyl ring substituents. Phenyl ring substituents are preferred in the para- or 4-ring position.

Rather than being independently chosen $R^2$ and $R^3$ can together form, along with the 3-position nitrogen atom of the thiourea, a heterocyclic nucleus forming a 5- or 6-membered ring. The ring atoms can be chosen from among nitrogen, carbon, oxygen, sulfur and selenium atoms. The ring necessarily contains at least one nitrogen atom. Exemplary rings include morpholino, piperidino, pyrrolidinyl, pyrrolinyl, thiomorpholino, thiazolidinyl, 4-thiazolinyl, selenazolidinyl, 4-selenazolinyl, imidazolidinyl, imidazolinyl, oxazolidinyl and 4-oxazolinyl rings. Specifically preferred rings are saturated or otherwise constructed to avoid electron withdrawal from the 3-position nitrogen atom.

To synthesize the 3,3-disubstituted acylhydrazinophenylthioureas of this invention, nitrophenylhydrazine can be employed as a starting material and can be used to form the desired 1-acyl-2-(aminophenyl)hydrazine using procedures that are generally described and specifically exemplified in Leone U.S. Pat. No. 4,030,925, here incorporated by reference.

A general procedure for synthesis using a 1-acyl-2-(aminophenyl)hydrazine as a starting material is to dissolve this material in acetone and to cool the resulting solution to $-78°$ C. in a dry ice-acetone bath. The 1-acyl-2-(aminophenyl)hydrazine is then reacted with 1,1'-thiocarbonyldiimidazole. The reaction mixture is allowed to warm to room temperature and then the solvent is removed. The remaining solid residue consists essentially of a mixture of a 2-acylhydrazinophenyl-isothiocyanate and imidazole. The solid is washed thoroughly with water to remove the imidazole, and the remaining material is recrystallized from acetone to give the 2-acylhydrazinophenylisothiocyanate separated from the imidazole. The isothiocyanate is then reacted in a suitable solvent, such as, ethanol or acetonitrile, with a secondary amine, where $R^2$ and $R^3$ are independent substituents, or a heterocyclic compound having a functionally equivalent nitrogen atom, where $R^2$ and $R^3$ together form a heterocyclic ring. After a few minutes reflux the 1-(2-acylhydrazinophenyl)-3,3-disubstituted thiourea separates from the solution as a precipitate. The solid product can be filtered off, washed with ether and dried for subsequent use.

This synthesis can be summarized as follows:

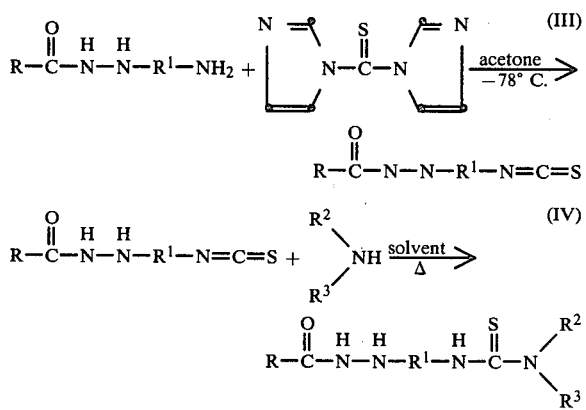

Where a thiocarbamoyl chloride is available which contains substituents corresponding to the desired $R^2$ and $R^3$ substituents, such as, dimethyl or diethyl carbamoyl chloride, an alternative synthetic route is to react the carbamoyl chloride with a desired 1-acyl-2-(aminophenyl)hydrazine in an inert solvent, such as acetonitrile, in the presence of a base, such as trimethylamine, under a nitrogen atmosphere at room temperature. The mixture is chilled and the product separates out of solution. The solid is filtered off and then stirred in warm water to remove hydrochloride salts. The remaining solid material represents the 3,3-disubstituted1-(acylhydrazinophenyl)thiourea.

This synthesis can be summarized as follows:

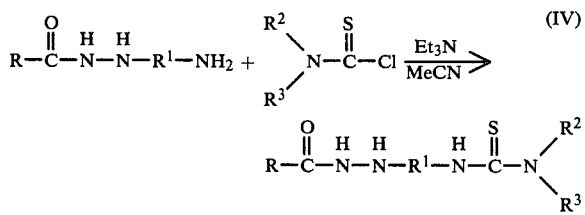

Illustrative specific 3,3-disubstituted acylhydrazinophenylthioureas useful in the practice of this invention include those set forth below in Table I.

TABLE I

| | |
|---|---|
| NA-1 | 1-[4-(2-formylhydrazino)phenyl]-3,3-dimethylthiourea |
| NA-2 | 1-[4-(2-formylhydrazino)phenyl]-3,3-di(chloroethyl)thiourea |
| NA-3 | 1-[2-(2-formylhydrazino)phenyl]-3,3-dimethylthiourea |
| NA-4 | 1-[3-(2-formylhydrazino)phenyl]-3,3-dimethylthiourea |

TABLE I-continued

| | |
|---|---|
| NA-5 | 1-[4-(2-acetylhydrazino)phenyl]-3,3-dimethylthiourea |
| NA-6 | 1-[4-(2-chloroacetylhydrazino)phenyl]-3,3-dimethylthiourea |
| NA-7 | 1-[4-(2-methoxyacetylhydrazino)phenyl]-3,3-dimethylthiourea |
| NA-8 | 1-[4-(2-heptanoylhydrazino)phenyl]-3,3-dimethylthiourea |
| NA-9 | 1-[4-(2-cyclobutanoylhydrazino)phenyl-3,3-dimethylthiourea |
| NA-10 | 1-{4-[2-(4-chlorobutanoyl)hydrazino]phenyl}-3,3-dimethylthiourea |
| NA-11 | 1-[4-(2-formylhydrazino)phenyl]-3,3-dibenzylthiourea |
| NA-12 | 1-[4-(2-acetylhydrazino)phenyl]-3,3-dibenzylthiourea |
| NA-13 | 1-{4-[2-(4-chlorobutanoyl)hydrazino]phenyl}-3,3-dibenzylthiourea |
| NA-14 | 1-[4-(2-formylhydrazino)phenyl]-3-methyl-3-phenylthiourea |
| NA-15 | 1-[4-(2-formylhydrazino)phenyl]-3,3-dibutylthiourea |
| NA-16 | 1-[4-(2-formylhydrazino)phenyl]-3-methyl-3-(2-ethoxy)ethylthiourea |
| NA-17 | 1-[4-(2-formylhydrazino)phenyl]-3,3-dihexylthiourea |
| NA-18 | 1-[4-(2-formylhydrazino)phenyl]-3,3-didodecylthiourea |
| NA-19 | 1-[4-(2-acetylhydrazino)phenyl]-3,3-dioctadecylthiourea |
| NA-20 | 1-[4-(2-bromoacetylhydrazino)]-3,3-dimethylthiourea |
| NA-21 | 4-[4-(2-formylhydrazino)phenylthiocarbamoyl]morpholine |
| NA-22 | 4-[4-(2-formylhydrazino)phenylthiocarbamoyl]thiomorpholine |
| NA-23 | 3-[4-(2-hydrazino)phenylthiocarbamoyl]thiazolidine |
| NA-24 | 3-[4-(2-formylhydrazino)phenylthiocarbamoyl]-4-thiazolidine |
| NA-25 | 1-[4-(2-formylhydrazino)phenylthiocarbamoyl]-3-pyrroline |
| NA-26 | 1-[4-(2-hydrazino)phenylthiocarbamoyl]pyrrolidine |
| NA-27 | 1-[ 4-(2-formylhydrazino)phenylthiocarbamoyl]imidazolidine |
| NA-28 | 1-[4-(2-fromylhydrazino)phenylthiocarbamoyl]-2-imidazoline |
| NA-29 | 3-[4-(2-formylhydrazino)phenylthiocarbamoyl]oxazolidine |
| NA-30 | 3-[4-(2-fromylhydrazino)phenylthiocarbamoyl]-4-oxazoline |
| NA-31 | 1-[4-(2-formylhydrazino)phenyl]-3,3-(di-2-naphthyl)thiourea |
| NA-32 | 1-[4-(2-formylhydrazino)phenylthiocarbamoyl]piperidine |
| NA-33 | 1-[4-(2-chloroacetylhydrazino)phenylthiocarbamoyl]piperidine |

The 3,3-disubstituted arylhydrazinophenylthiourea nucleating agents can be employed with any conventional photographic element capable of forming a direct-positive image containing, coated on a photographic support, at least one silver halide emulsion layer containing a vehicle and silver halide grains capable of forming an internal latent image upon exposure to actonic radiation. As employed herein, the terms "internal latent image silver halide grains" and "silver halide grains capable of forming an internal latent image" are employed in the artrecognized sense of designating silver halide grains which produce substantially higher optical densities when coated, imagewise exposed and developed in an internal developer than when comparably coated, exposed and developed in a surface developer. Preferred internal latent image silver halide grains are those which, when examined according to normal photographic testing techniques, by coating a test portion on a photographic support (e.g., at a coverage of from 3 to 4 grams per square meter), exposing to a light intensity scale (e.g., with a 500-watt tungsten lamp at a distance of 61 cm) for a fixed time (e.g., between $1 \times 10^{-2}$ and 1 second) and developing for 5 minutes at 25° C. in Kodak Developer DK-50 (a surface developer), provide a density of at least 0.5 less than when this testing procedure is repeated, substituting for the surface developer Kodak Developer DK-50 containing 0.5 gram per liter of potassium iodide (an internal developer). The internal latent image silver halide grains most preferred for use in the practice of this invention are those which, when tested using an internal developer and a surface developer as indicated above, produce an optical density with the internal developer at least 5 times that produced by the surface developer. It is additionally preferred that the internal latent image silver halide grains produce an optical density of less than 0.4 and most preferably, less than 0.25 when coated, exposed and developed in surface developer as indicated above, that is, the silver halide grains are preferably initially substantially unfogged and free of latent image on their surface.

The surface developer referred to herein as Kodak Developer DK-50 is described in the *Handbook of Chemistry and Physics*, 30th edition, 1947, Chemical Rubber Publishing Company, Cleveland, Ohio, page 2558, and has the following composition:
Water, about 125° F. (52° C.): 500.0 cc
N-methyl-p-aminophenol sulfate: 2.5 g
Sodium sulfite, desiccated: 30.0 g
Hydroquinone: 2.5 g
Sodium metaborate: 10.0 g
Potassium bromide: 0.5 g
Water to make: 1.0 liter.

Internal latent image silver halide grains which can be employed in the practice of this invention are well known in the art. Patents teaching the use of internal latent image silver halide grains in photographic emulsions and elements include Davey et al U.S. Pat. No. 2,592,250, Porter et al U.S. Pat. No. 3,206,313, Milton U.S. Pat. No. 3,761,266, Ridgway U.S. Pat. No. 3,586,505, Gilman et al U.S. Pat. No. 3,772,030, Gilman et al U.S. Pat. No. 3,761,267, and Evans U.S. Pat. No. 3,761,276, the disclosures of which are hereby incorporated by reference.

The internal latent image silver halide grains preferably contain bromide as the predominant halide. The silver bromide grains can consist essentially of silver bromide or can contain silver bromoiodide, silver chlorobromide, silver chlorobromoiodide crystals and mixtures thereof. Internal latent image-forming sites can be incorporated into the grains by either physical or chemical internal sensitization. Davey et al, cited above, for example, teaches the physical formation of internal latent image-forming sites by the halide conversion technique. Chemical formation of internal latent image-forming sites can be produced through the use of sulfur, gold, selenium, tellurium and/or reduction sensitizers of the type described, for example, in Sheppard et al U.S. Pat. No. 1,623,499, Waller et al U.S. Pat. No. 2,399,083, McVeigh U.S. Pat. No. 3,297,447, and Dunn U.S. Pat. No. 3,297,446, as taught in the patents cited in the preceding paragraph. Internal latent image sites can also be formed through the incorporation of metal dopants, particularly Group VIII nobel metals, such as, ruthenium, rhodium, palladium, iridium, osmium and platinum, as taught by Berriman U.S. Pat. No. 3,367,778.

The preferred foreign metal ions are polyvalent metal ions which include the above-noted Group VIII dopants, as well as polyvalent metal ions, such as, lead, antimony, bismuth, arsenic and the like. In highly preferred embodiments, the silver halide grains are formed in the presence of bismuth, lead or iridium ions. In a preferred approach, the internal latent image sites can be formed within the silver halide grains during precipitation of silver halide. In an alternate approach, a core grain can be formed which is treated to form the internal image sites and then a shell deposited over the core grains, as taught by Porter et al, cited above.

The silver halide grains employed in the practice of this invention are preferably monodispersed, and in some embodiments are preferably large-grain emulsions made according to Wilgus German OLS No. 2,107,118, which is incorporated herein by reference. The monodispersed emulsions are those which comprise silver halide grains having a substantially uniform diameter. Generally, in such emulsions, no more than about 5 percent by number of the silver halide grains smaller than the mean grain size and/or no more than about 5 percent by number of the silver halide grains larger than the mean grain size vary in diameter from the mean grain diameter by more than about 40 percent. Preferred photographic emulsions of this invention comprise silver halide grains, at least 95 percent by weight of said grains having a diameter which is within 40 percent and preferably within about 30 percent of the mean grain diameter. Mean grain diameter, i.e., average grain size, can be determined using conventional methods, e.g, such as projective area, as shown in an article by Trivelli et al entitled "Empirical Relations Between Sensitometric and Size-Frequency Characteristics in Photographic Emulsion Series" in *The Photographic Journal*, Volume LXXIX, 1939, pages 330 through 338. The aforementioned uniform size distribution of silver halide grains is a characteristic of the grains in monodispersed photographic silver halide emulsions. Silver halide grains having a narrow size distribution can be obtained by controlling the conditions at which the silver halide grains are prepared using a double run procedure. In such a procedure, the silver halide grains are prepared by simultaneously running an aqueous solution of a silver salt, such as silver nitrate, and an aqueous solution of a water-soluble halide, for example, an alkali metal halide, such as potassium bromide, into a rapidly agitated aqueous solution of a silver halide peptizer, preferably gelatin, a gelatin derivative or some other protein peptizer. Suitable methods for preparing photographic silver halide emulsions having the required uniform particle size are disclosed in an article entitled "Ia: Properties of Photographic Emulsion Grains", by Klein and Moisar, *The Journal of Photographic Science*, Volume 12, 1964, pages 242 through 251; an article entitled "The Spectral Sensitization of Silver Bromide Emulsions on Different Crystallographic Faces", by Markocki, *The Journal of Photographic Science*, Volume 13, 1965, pages 85 through 89; an article entitled "Studies on Silver Bromide Sols, Part I. The Formation and Aging of Monodispersed Silver Bromide Sols", by Ottewill and Woodbridge, *The Journal of Photographic Science*, Volume 13, 1965, pages 98 through 103; and an article entitled "Studies on Silver Bromide Sols, Part II. The Effect of Additives on the Sol Particles", by Ottewill and Woodbridge, *The Journal of Photographic Science*, Volume 13, 1965, pages 104 through 107.

Where internal latent image sites have been formed through internal chemical sensitization or the use of metal dopants, the surface of the silver halide grains can be sensitized to a level below that which will produce substantial density in a surface developer; that is, less than 0.4 (preferably less than 0.25) when coated, exposed and surface developed as described above. The silver halide grains are preferably predominantly silver bromide grains chemically surface sensitized to a level which would provide a maximum density of at least 0.5 using undoped silver halide grains of the same size and halide composition when coated, exposed and developed as described above.

Surface chemical sensitization can be undertaken using techniques such as those disclosed by Sheppard, Waller et al, McVeigh or Dunn, cited above. The silver halide grains can also be surface sensitized with salts of the noble metals, such as, ruthenium, palladium, and platinum. Representative compounds are ammonium chloropalladate, potassium chloroplatinate and sodium chloropalladite, which are used for sensitizing in amounts below that which produces any substantial fog inhibition, as described in Smith et al U.S. Pat. No. 2,448,060, and as antifoggants in higher amounts, as described in Trivelli et al U.S. Pat. Nos. 2,566,245 and 2,566,263. The silver halide grains can also be chemically sensitized with reducing agents, such as stannous salts (Carroll U.S. Pat. No. 2,487,850, polyamines, such as diethylene triamine (Lowe et al U.S. Pat. No. 2,518,698), polyamines, such as spermine (Lowe et al U.S. Pat. No. 2,521,925), or bis($\beta$-aminoethyl)sulfide and its water-soluble salts (Lowe et al U.S. Pat. No. 2,521,926).

The photographic silver halide emulsion layers and other layers of the photographic elements can contain various colloids alone or in combination as vehicles. Suitable hydrophilic materials include both naturally occurring substances, such as, proteins, protein derivatives, cellulose derivatives, e.g., cellulose esters, gelatin, e.g., alkali-treated gelatin (cattle bone or hide gelatin) or acid-treated gelatin (pigskin gelatin), gelatin derivatives, e.g., acetylated gelatin, phthalated gelatin and the like, polysaccharides, such as, dextran, gum arabic, zein, casein, pectin, collagen derivatives, collodion, agar-agar, arrowroot, albumin and the like, as described in Yutzy U.S. Pat. Nos. 2,614,928 and '919, Lowe et al U.S. Pat. Nos. 2,691,582, 2,614,930 and '931, 2,327,808, and 2,448,534, Gates et al U.S. Pat. Nos. 2,787,545 and 2,956,880, Himmelmann et al U.S. Pat. No. 3,061,436, Farrell et al U.S. Pat. No. 2,816,027, Ryan U.S. Pat. Nos. 3,132,945, 3,138,461, and 3,186,846, Dersch et al U.K. Pat. No. 1,167,159 and U.S. Pat. Nos. 2,960,405 and 3,436,220, Geary U.S. Pat. No. 3,486,896, Gazzard U.K. Pat. No. 793,549, Gates et al U.S. Pat. Nos. 2,992,213, 3,157,506, 3,184,312, and 3,539,353, Miller et al U.S. Pat. No. 3,227,571, Boyer et al U.S. Pat. No. 3,532,502, Malan U.S. Pat. No. 3,551,151, Lohmer et al U.S. Pat. No. 4,018,609, Luciani et al U.K. Pat. No. 1,186,790, Hori et al U.K. Pat. No. 1,489,080 and Belgian Pat. No. 856,631, U.K. Pat. No. 1,490,644, U.K. Pat. No. 1,483,551, Arase et al U.K. Pat. No. 1,459,906, Salo U.S. Pat. Nos. 2,110,491 and 2,311,086, Fallesen U.S. Pat. No. 2,343,650, Yutzy U.S. Pat. No. 2,322,085, Lowe U.S. Pat. No. 2,563,791, Talbot et al U.S. Pat. No. 2,725,293, Hilborn U.S. Pat. No. 2,748,022, DePauw et al U.S. Pat. No. 2,956,883, Ritchie U.K. Pat. No. 2,095, DeStubner U.S. Pat. No. 1,752,069, Sheppard et al U.S. Pat. No. 2,127,573, Lierg U.S. Pat. No. 2,256,720, Gaspar U.S. Pat. No. 2,361,936, Farmer U.K. Pat. No. 15,727, Stevens U.K. Pat. No. 1,062,116, and Yamamoto et al U.S. Pat. No. 3,923,517.

Photographic emulsion layers, and other layers of photographic elements, such as, overcoat layers, interlayers, and subbing layers, as well as receiving layers in image-transfer elements, can also contain alone or in combination with hydrophilic water-permeable colloids as vehicles or vehicle extenders (e.g., in the form of latices), synthetic polymeric peptizers, carriers and/or binders, such as, poly(vinyl lactams), acrylamide polymers, polyvinyl alcohol, and its derivatives, polyvinyl acetals, polymers of alkyl, and sulfoalkyl acrylates, and methacrylates, hydrolyzed polyvinyl acetates, polyamides, polyvinyl pyridine, acrylic acid polymers, maleic anhydride copolymers, polyalkylene oxides, methacrylamide copolymers, polyvinyl oxazolidinones, maleic acid copolymers, vinylamine copolymers, methacrylic acid copolymers, acryloyloxyalkylsulfonic acid copolymers, sulfoalkylacrylamide copolymers, polyalkyleneimine copolymers, polyamines, N,N-dialkylaminoalkyl acrylates, vinyl imidazole copolymers, vinyl sulfide copolymers, halogenated styrene polymers, aminea-crylamide polymers, polypeptides and the like, as described in Hollister et al U.S. Pat. Nos. 3,679,425, 3,706,564, and 3,813,251, Lowe U.S. Pat. Nos. 2,253,078, 2,276,322 and '323, 2,281,703, 2,311,058 and 2,414,207, Lowe et al U.S. Pat. Nos. 2,484,456, 2,541,474, and 2,632,704, Perry et al U.S. Pat. No. 3,425,836, Smith et al U.S. Pat. Nos. 3,415,653 and 3,615,624, Smith U.S. Pat. No. 3,488,708, Whiteley et al U.S. Pat. Nos. 3,392,025 and 3,511,818, Fitzgerald U.S. Pat. Nos. 3,681,079, 3,721,565, 3,852,073, 3,861,918, and 3,925,083, Fitzgerald et al U.S. Pat. No. 3,879,205, Nottorf U.S. Pat. No. 3,142,568, Houck et al U.S. Pat. Nos. 3,062,674 and 3,220,844, Dann et al U.S. Pat. No. 2,882,161, Schupp U.S. Pat. No. 2,579,016, Weaver U.S. Pat. No. 2,829,053, Alles et al U.S. Pat. No. 2,698,240, Priest et al U.S. Pat. No. 3,003,879, Merrill et al U.S. Pat. No. 3,419,397, Stonham U.S. Pat. No. 3,284,207, Lohmer et al U.S. Pat. No. 3,167,430, Williams U.S. Pat. No. 2,957,767, Dawson et al U.S. Pat. No. 2,893,867, Smith et al U.S. Pat. Nos. 2,860,986 and 2,904,549, Ponticello et al U.S. Pat. Nos. 3,929,482 and 3,860,428, Ponticello U.S. Pat. No. 3,939,130, Dykstra U.S. Pat. No. 3,411,911, Dykstra et al Canadian Pat. No. 774,054, Ream et al U.S. Pat. No. 3,287,289, Smith U.K. Pat. No. 1,466,600, Stevens U.K. Pat. No. 1,062,116, Fordyce U.S. Pat. No. 2,211,323, Martinez U.S. Pat. No. 2,284,877, Watkins U.S. Pat. No. 2,420,455, Jones U.S. Pat. No. 2,533,166, Bolton U.S. Pat. No. 2,495,918, Graves U.S. Pat. No. 2,289,775, Yackel U.S. Pat. No. 2,565,418, Unruh et al U.S. Pat. Nos. 2,865,893 and 2,875,059, Rees et al U.S. Pat. No. 3,536,491, Broadhead et al U.K. Pat. No. 1,348,815, Taylor et al U.S. Pat. No. 3,479,186, Merrill et al U.S. Pat. No. 3,520,857, Bacon et al U.S. Pat. No. 3,690,888, Bowman U.S. Pat. No. 3,748,143, Dickinson et al U.K. Pat. Nos. 808,227 and '228, Wood U.K. Pat. No. 822,192, and Iguchi et al U.K. Pat. No. 1,398,055.

The layers of the photographic elements can be coated on a variety of supports. Typical photographic supports include polymeric film, wood fiber, e.g., paper, metallic sheet and foil, glass and ceramic supporting elements provided with one or more subbing layers to enhance the adhesive, antistatic, dimensional, abrasive, hardness, frictional, antihalation, and/or other properties of the support surface.

Typical of useful polymeric film supports are films of cellulose nitrate and cellulose esters, such as, cellulose triacetate and diacetate, polystyrene, polyamides, homo-polymers and co-polymers of vinyl chloride, poly(vinyl acetal), polycarbonate, homo-polymers and co-polymers of olefins, such as, polyethylene and polypropylene, and polyesters of dibasic aromatic carboxylic acids with divalent alcohols, such as poly(ethylene terephthalate).

Typical of useful paper supports are those which are partially acetylated or coated with baryta and/or a polyolefin, particularly a polymer of an α-olefin containing 2 to 10 carbon atoms, such as, polyethylene, polypropylene, copolymers of ethylene and propylene.

Polyolefins, such as, polyethylene, polypropylene and polyallomers, e.g., copolymers of ethylene with propylene, as illustrated by Hagemeyer et al U.S. Pat. No. 3,478,128, are preferably employed as resin coatings over paper, as illustrated by Crawford et al U.S. Pat. No. 3,411,908 and Joseph et al U.S. Pat. No. 3,630,740, over polystyrene and polyester film supports, as illustrated by Crawford et al U.S. Pat. No. 3,630,742, or can be employed as unitary flexible reflection/supports, as illustrated by Venor et al U.S. Pat. No. 3,973,963.

Preferred cellulose ester supports are cellulose triacetate supports, as illustrated by Fordyce et al U.S. Pat. Nos. 2,492,977, '978, and 2,739,069, as well as mixed cellulose ester supports, such as, cellulose acetate propionate and cellulose acetate butyrate, as illustrated by Fordyce et al U.S. Pat. No. 2,739,070.

Preferred polyester film supports are comprised of linear polyester, such as illustrated by Alles et al U.S. Pat. No. 2,627,088, Wellman U.S. Pat. No. 2,720,503, Alles U.S. Pat. No. 2,779,684, and Kibler et al U.S. Pat. No. 2,901,466. Polyester films can be formed by varied techniques, as illustrated by Alles, cited above, Czerkas et al U.S. Pat. No. 3,663,683, and Williams et al U.S. Pat. No. 3,504,075, and modified for use as photographic film supports, as illustrated by Van Stappen U.S. Pat. No. 3,227,576, Nadeau et al U.S. Pat. No. 3,501,301, Reedy et al U.S. Pat. No. 3,589,905, Babbitt et al U.S. Pat. No. 3,850,640, Bailey et al U.S. Pat. No. 3,888,678, Hunter U.S. Pat. No. 3,904,420, and Mallinson et al U.S. Pat. No. 3,928,697.

The photographic elements can employ supports which are resistant to dimensional change at elevated temperatures. Such supports can be comprised of linear condensation polymers which have glass transition temperatures above about 190° C., preferably 220° C., such as, polycarbonates, polycarboxylic esters, polyamides, polysulfonamides, polyethers, polyimides, polysulfonates and copolymer variants, as illustrated by Hamb U.S. Pat. Nos. 3,634,089 and 3,772,405, Hamb et al U.S. Pat. Nos. 3,725,070 and 3,793,249, Wilson *Research Disclosure*, Volume 118, February 1974, Item 11833, and Volume 120, April 1974, Item 12046, Conklin et al *Research Disclosure*, Volume 120, April 1974, Item 12012, *Product Licensing Index*, Volume 92, December 1971, Items 9205 and 9207, *Research Disclosure*, Volume 101, September 1972, Items 10119 and 10148, *Research Disclosure*, Volume 106, February 1973, Item 10613, *Research Disclosure*, Volume 117, January 1974, Item 11709, and *Research Disclosure*, Volume 134, June 1975, Item 13455. Both *Research Disclosure* and *Product Licensing Index* are published by Industrial Opportunities, Ltd., Homewell, Havant, Hampshire, PO9 1EF, United Kingdom.

The 3,3-disubstituted arylhydrazinophenylthiourea nucleating agents of this invention can be employed in any desired concentration that will permit a degree of selectivity in developing imagewise silver halide grains capable of forming an internal latent image, which grains have not been imagewise exposed, as compared to silver halide grains containing an internal latent image formed by imagewise exposure.

In a preferred form of this invention, the 3,3-disubstituted arylhydrazinophenylthiourea nucleating agents are adsorbed to the surface of the internal latent image silver halide grains and employed in concentrations ranging from 0.1 to 500 mg of adsorbed nucleating agent per mole of silver. Preferably, 1 to 100 mg of adsorbed nucleating agent per mole of silver is employed. Optimum concentrations can, of course, vary somewhat from one applicateon to another. Where the 3,3-disubstituted arylhydrazinophenylthiourea nucleating agent is to be adsorbed to the surface of the silver halide grains, it can be adsorbed using the procedures well known to those skilled in the art for adsorbing sensitizing dyes, such as cyanine and merocyanine dyes, to the surface of silver halide grains.

A simple exposure and development process can be used to form a direct-positive image. In one embodiment, a photographic element comprising at least one layer of a silver halide emulsion as described above can be imagewise exposed and then developed in a silver halide surface developer.

It is understood that the term "surface developer" encompasses those developers which will reveal the surface latent image on a silver halide grain, but will not reveal substantial internal latent image in an internal image-forming emulsion, and under the conditions generally used develop a surface-sensitive silver halide emulsion. The surface developers can generally utilize any of the silver halide developing agents or reducing agents, but the developing bath or composition is generally substantially free of a silver halide solvent (such as, water-soluble thiocyanates, water-soluble thioethers, thiosulfates, ammonia) which will disrupt or dissolve the grain to reveal substantial internal image. Low amounts of excess halide are sometimes desirable in the developer or incorporated in the emulsion as halide-releasing compounds, but high amounts of iodide or iodide-releasing compounds are generally avoided to prevent substantial disruption of the grain. Typical silver halide developing agents which can be used in the developing compositions of this invention include hydroquinones, catechols, aminophenols, 3-pyrazolidones, ascorbic acid and its derivatives, reductones, phenylenediamines, or combinations thereof. Illustrative of useful surface developers are those disclosed in Ives U.S. Pat. No. 2,563,785, Evans U.S. Pat. No. 3,761,276, Knott et al U.S. Pat. No. 2,456,953, and Juoy U.S. Pat. No. 3,511,662.

Where the developing agents are initially entirely incorporated in the photographic elements, the remaining components (e.g., water, activators to adjust pH, preservatives, etc.) normally present in surface developers constitute what is commonly referred to as an activator solution. Except for the omission of the developing agent, activator solutions are identical to developer solutions in composition and are employed identically with incorporated developing agent photographic elements. Subsequent references to developing compositions are inclusive of both developer and activator solutions.

Photographic elements containing monosubstituted acylhydrazinophenylthioureas have been employed in combination with developing compositions having a pH at or above 13.5. At lower pH levels the nucleating activity of mono-substituted acylhydrazinophenylthioureas is significantly diminished. It is a distinct advantage of the present invention that the 3,3-disubstituted acylhydrazinophenylthioureas retain to a relatively high degree their nucleating activity when employed with developing compositions at pH levels down to and below 12.0. In addition to being useful at higher pH levels conventionally employed with monosubstituted acylhydrazinophenylthioureas, typically in the range of from 13.5 to 13.9, the 3,3-disubstituted acylhydrazinophenylthioureas are useful at pH levels as low as 11.8 and, depending upon the specific form of the photographic element employed, even lower. It is frequently desirable to lower developing composition pH levels to reduce the potential hazard which the higher pH levels entail if the developing compositions are carelessly or otherwise improperly handled. For such applications, it is specifically preferred to employ developing compositions in the lower pH ranges, of from about 12.0 to 13.0, in processing photographic elements according to this invention containing 3,3-disubstituted acylphenylhydrazinophenylthioureas.

The developing compositions used in the process of this invention can contain certain antifoggants and development restrainers, or, optionally, they can be incorporated in layers of the photographic element. For example, in some applications, improved results can be obtained when the direct-positive emulsions are processed in the presence of certain antifoggants, as disclosed in Stauffer U.S. Pat. No. 2,497,917, which is incorporated herein by reference.

Typical useful antifoggants include benzotriazoles, such as, benzotriazole, 5-methylbenzotriazole, 5-ethylbenzotriazole, benzimidazoles, such as, 5-nitrobenzimidazole, benzothiazoles, such as, 5-nitrobenzothiazole, 5-methylbenzothiazole, heterocyclic thiones, such as, 1-methyl-2-tetrazoline-5-thione, triazines, such as, 2,4-dimethylamino-6-chloro-5-triazine, benzoxazoles, such as, ethylbenzoxazole, and pyrroles, such as, 2,5-dimethylpyrrole.

In certain embodiments, good results are obtained when the elements are processed in the presence of high levels of the antifoggants mentioned above. When antifoggants such as benzotriazoles are used, good results can be obtained when the processing solution contains from 500 mg to 10 grams per liter and preferably 1 to 5 grams per liter; when they are incorporated in the photographic element, concentrations of from 5 to 500 mg per mole of Ag and preferably concentrations of 10 to 150 mg per mole of Ag are employed. Optimum antifoggant concentrations are a function of the specific antifoggant, element, and processing solution employed.

The essential features of the 3,3-disubstituted arylhydrazinophenylthiourea nucleating agents of this invention and the silver halide emulsions and photographic elements in which they are incorporated, as well as procedures for their use and processing, are described above. It is appreciated that, in preferred photographic applications, the emulsions and elements can contain additional features which are in themselves well known to those familiar with the photographic arts. Further, these applications can entail conventional modifications in the procedures described above. A variety of such features are disclosed in *Research Disclosure*, Volume 176, December 1978, Item 17643, the disclosure of which is herein incorporated by reference, particularly Paragraph II, Emulsion washing; Paragraph IV, Spectral sensitization and Desensitization; Paragraph V, Brighteners; Paragraph VI, Antifoggants and stabilizers; Paragraph VIII, Absorbing and scattering materials; Paragraph X, Hardeners; Paragraph XI, Coating aids; Paragraph XII, Plasticizers and lubricants; Paragraph XIII, Antistatic layers; Paragraph XIV, Methods of addition; Paragraph XV, Coating and drying Procedures; Paragraph XVI, Matting agents; Paragraph XVIII, Exposure; Paragraph XX, Developing agents; and Paragraph XXI, Development modifiers.

It is specifically contemplated to employ in combination with 3,3-disubstituted acylhydrazinophenylthiourea nucleating agents other conventional nucleating agents. In a specifically preferred form one or a combination of 3,3-disubstituted acylhydrazinophenylthiourea nucleating agents are employed at a concentration of up to about 200 mg per mole of silver, as indicated above, in combination with a conventional substituted hydrazine type nucleating agent which is present in a concentration of from about 200 mg to about 2 grams per mole of silver. Where the 3,3-disubstituted acylhydrazinophenylthiourea nucleating agent actually increases photographic speed, with increasing processing temperatures, using the nucleating agent in combination with a conventional nucleating agent which decreases photographic speed with increasing processing temperatures, can result in a surprising degree of temperature insensitivity for the speed and developability of the resulting photographic emulsion.

In one preferred form of this invention the 3,3-disubstituted acylhydrazinophenylthiourea nucleating agents are employed in combination with hydrazide and hydrazone nucleating agents of the type disclosed by Whitmore, cited above. Such hydrazides and hydrazones are nitrogen-containing compounds having the formulas

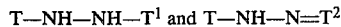

T—NH—NH—T$^1$ and T—NH—N=T$^2$ wherein T is an aryl radical and including a substituted aryl radical, T$^1$ is an acyl or a sulfonyl radical, and T$^2$ is an alkylidene radical and including substituted alkylidene radicals. Typical aryl radicals for the substituent T have the formula M—T$^3$—, wherein T$^3$ is an aryl radical (such as, phenyl, 1-naphthyl, 2-naphthyl, etc.) and M can be such substituents as hydroogen, hydroxy, amino, alkyl, alkylamino, arylamino, heterocyclic amino (amino containing a heterocyclic moiety), alkoxy, aryloxy, acyloxy, arylcarbonamido, alkylcarbonamido, heterocyclic carbonamido (carbonamido containing a heterocyclic moiety), arylsulfonamido, alkylsulfonamido, and heterocyclic sulfonamido (sulfonamido containing a hyeterocyclic moiety). Typical acyl and sulfonyl radicals for the substituent T$^1$ have the formula

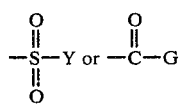

wherein Y can be such substituents as alkyl, aryl, and heterocyclic radicals, G can represent a hydrogen atom or the same substituent as Y as well as radicals having the formula

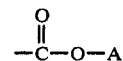

to form oxalyl radicals wherein A is an alkyl, aryl or a heterocyclic radical. Typical alkylidene radicals for the substituent T$^2$ have the formula =C—D$^2$ wherein D can be a hydrogen atom or such radicals as alkyl, aryl, and heterocyclic radicals. Typical aryl substituents for the above-described hydrazides and hydrazones include phenyl, naphthyl, diphenyl, and the like. Typical heterocyclic substituents for the above-described hydrazides and hydrazones include azoles, azines, furan, thiophene, quinoline, pyrazole, and the like. Typical alkyl (or alkylidene) substituents for the above-described hydrazides and hydrazones have 1 to 22 carbon atoms including methyl, ethyl, isopropyl, n-propyl, isobutyl, n-butyl, t-butyl, amyl, n-octyl, n-decyl, n-dodecyl, n-octadecyl, n-eicosyl, n-docosyl, etc.

Illustrative specific hydrazide (named as hydrazine derivatives) and hydrazone nucleating agents useful in the practice of this invention include those set forth below in Table II.

TABLE II

| | |
|---|---|
| H-1 | 1-acetyl-2-phenylhydrazine |
| H-2 | 1-acetyl-2-(4-hydroxyphenyl)hydrazine |
| H-3 | 1-acetyl-2-(4-aminophenyl)hydrazine |
| H-4 | 1-acetyl-2-(4-methylphenyl)hydrazine |
| H-5 | 1-acetyl-2-(4-acetamidophenyl)hydrazine |
| H-6 | 1-acetyl-2-(4-benzamidophenyl)hydrazine |
| H-7 | 1-acetyl-2-(4-methoxyphenyl)hydrazine |
| H-8 | 1-acetyl-2-[4-(3-sulfobenzamido)phenyl]hydrazine |
| H-9 | 1-acetyl-2-(4-phenylsulfamidophenyl)hydrazine |
| H-10 | 1-acetyl-2-(4-methylsulfonamidophenyl)hydrazine |
| H-11 | 1-phenylsulfonyl-2-phenylhydrazine |
| H-12 | 1-methylsulfonyl-2-phenylhydrazine |
| H-13 | 1-benzoyl-2-phenylhydrazine |
| H-14 | 1-benzoyl-2-(4-benzamidophenyl)hydrazine |
| H-15 | 1-ethoxyalyl-2-phenylhydrazine |
| H-16 | 1-methoxysulfonyl-2-(3-phenylsulfonamidophenyl)hydrazine |
| H-17 | 1-(4-acetamidophenylsulfonyl)-2-(1-naphthyl)hydrazine |
| H-18 | 1-ethylsulfonyl-2-(4-diethylaminophenyl)hydrazine |
| H-19 | 1-phenylsulfonyl-2-(4-benzamido-2,5-diethoxyphenyl)hydrazine |
| H-20 | 5-(1-carbo-2-phenylhydrazino)-1-phenyl-3-pyrazolidone |
| H-21 | 2-(1-carbo-2-phenylhydrazino)furan |
| H-22 | 4-(1-carbo-2-phenylhydrazino)pyridine |
| H-23 | 2-(1-carbo-2-phenylhydrazino)benzothiazole |
| H-24 | 1-[2-(2,4-di-tert-amylphenoxy)-5-(3,5-disulfobenzamido)benzoyl]-2-phenylhydrazine |
| H-25 | 1-acetyl-2-{4-[5-amino-2-(2,4-di-tert-pentyl-phenoxy)benzamido]phenyl}hydrazine |
| H-26 | 1-lauroyl-2-phenylhydrazine |
| H-27 | 1-lauroyl-2-[4-(3-sulfobenzamido)phenyl]hydrazine |
| H-28 | 1-methylsulfonyl-2-(4-octadecylphenyl)hydrazine |
| H-29 | 1-octadecyloxalyl-2-phenylhydrazine |
| H-30 | 1-octadecyloxalyl-2-[4-(3-sulfobenzamido)phenyl]hydrazine |
| H-31 | 1-lauroyl-2-[4-(β-methylsulfonamidoethyl)phenyl]hydrazine |
| H-32 | 1-[3-(2,4-di-tert-amyl-χ-sulfophenoxy)benzoyl]-2-phenylhydrazine |
| H-33 | 5-{1-carbo-2-[4-(α-sulfostearamido)phenyl[hydrazino}-1-phenyl-3-pyrazolidone |
| H-34 | formaldehyde phenylhydrazone |
| H-35 | formaldehyde 4-(β-methylsulfonamidoethyl)phenylhydrazone |
| H-36 | mucochloric acid 4-(β-methylsulfonamidoethyl)phenylhydrazone |
| H-37 | acetone 4-methylphenylhydrazone |
| H-38 | benzaldehyde 4-(β-methylsulfonamidoethyl)phenylhydrazone |

TABLE II-continued

| | |
|---|---|
| H-39 | benzaldehyde 4-methoxyphenylhydrazone |
| H-40 | benzaldehyde 4-(3-sulfobenzamido)phenylhydrazone |
| H-41 | formaldehyde 4-methylsulfonamidodphenylhydrazone |
| H-42 | acetaldehyde 4-phenylsulfonamidophenylhydrazone |
| H-43 | p-tolualdehyde 4-diethylaminophenylhydrazone |
| H-44 | cinchoninaldehyde 4-acetamidophenylhydrazone |
| H-45 | 2-furaldehyde 4-methylsulfonamido-1-naphthylhydrazone |
| H-46 | 1-[4-(2-formylhydrazino)phenyl]-3-n-hexylurea |
| H-47 | hendecanal 4-(α-sulfostearamido)phenylhydrazone |
| H-48 | 3-octadecyloxybenzaldehyde phenylhydrazone |
| H-49 | 3-octadecyloxybenzaldehyde 4(4-sulfobenzamido)phenylhydrazone |
| H-50 | benzaldehyde 4-[5-(3,5-disulfo)-2-(2,4-di-tert-pentyl-phenoxy)benzamido]phenylhydrazone dipotassium salt |
| H-51 | oxyguargum 4-(β-methylsulfonamidoethyl)-phenylhydrazone |
| H-52 | 1-phenylacetyl-2-phenylhydrazine |
| H-53 | 1-formyl-2-p-tolylhydrazine |

In another preferred form of this invention the 3,3-disubstituted acylhydrazinophenylthiourea nucleating agents are employed in combination with N-substituted cycloammonium salts of the type disclosed by Kurtz et al U.S. Pat. Nos. 3,719,494 and 3,734,738 and Lincoln et al U.S. Pat. Nos. 3,615,615 and 3,759,901. Generally, these compounds can be represented by the formula

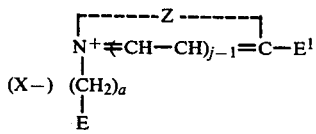

wherein
Z represents the atoms necessary to complete a heterocyclic nucleus containing a heterocyclic ring of 5 to 6 atoms including the quaternary nitrogen atom, with the additional atoms of the heterocyclic ring being selected from carbon, nitrogen, oxygen, sulfur and selenium,
j represents a positive integer of from 1 to 2,
a represents a positive integer of from 2 to 6,
$X^\ominus$ represents an acid anion,
E represents a member selected from (a) a formyl radical, (b) a radical having the formula

wherein each of $L^1$ and $L^2$, when taken alone, represents a member selected from an alkoxy radical and an alkylthio radical, and $L^1$ and $L^2$, when taken together, represent the atoms necessary to complete a cyclic radical selected from cyclic oxyacetals and cyclic thioacetals having from 5 to 6 atoms in the heterocyclic acetal ring, and (c) a 1-hydrazonoalkyl radical, and
$E^1$ represents either a hydrogen atom, an alkyl radical, an aralkyl radical, an alkylthio radical or, an aryl radical such as phenyl or naphthyl, and including substituted aryl radicals.

In certain preferred embodiments of this invention, the N-substituted cycloammonium quaternary salts are those which contain N-substituted alkyl radicals having the terminal carbon atom substituted with a hydrazono radical, an acyl radical such as a formyl radical, an acetyl radical or a benzoyl radical, and those which have a dihydro-aromatic ring nucleus, such as, for example, a dihydropyridinium nucleus.

Illustrative specific N-substituted quaternary ammonium salt nucleating agents useful in the practice of this invention include those set forth below in Table III.

TABLE III

| | |
|---|---|
| QAS-1 | 3-(2-formylethyl)-2-methylbenzothiazolium salt |
| QAS-2 | 3-(2-formylethyl)-2-methylnaphtho[2,3-d]-thiazolium salt |
| QAS-3 | 3-(2-acetylethyl)-2-phenoxymethylbenzothiazolium salt |
| QAS-4 | 3-(2-acetylethyl)-2-benzoselenazolium salt |
| QAS-5 | 1,2-dihydro-3-methyl-4-phenylpyrido[2,1-b]-benzothiazolium salt |
| QAS-6 | 1,2-dihydro-3-methyl4-phenylpyrido[2,1-b]-5-phenylbenzoxazolium salt |
| QAS-7 | 1,2-dihydro-3,4-dimethylpyrido[2,1-b]benzothiazolium salt |
| QAS-8 | 1,2-dihydro-3,4-diphenylpyrido[2,1-b]benzothiazolium salt |
| QAS-9 | 1,2-dihydro-2-butyl-3-methyl-4-phenyl-pyrido[2,1-b]-5-carbethoxybenzothiazolium salt |
| QAS-10 | 1,2-dihydro-3-methyl-4-phenylpyrido-benzothiazolium salt |
| QAS-11 | 1,2-dihydro-3,4-dimethylpyrido[2,1-b]-5-(N-ethyl-N-octadecylcarbamido)benzothiazolium salt |
| QAS-12 | 3-(3,3-di(ethylthio)pyrpyl]-2-methylbenzothiazolium iodide |
| QAS-13 | 1-(2-formylethyl)lepidinum bromide |
| QAS-14 | 3-[3,3-di(ethyl)propyl]-2-methylbenzothiazolium iodide |
| QAS-15 | 3-(6,6-diethoxy-n-hexyl)-2-methylnaphtho[2,1-d]-thiazolium bromide |
| QAS-16 | 3-[2-(1,3-dioxan-2-yl)ethyl]-2-methylbenzoselenazolium bromide |
| QAS-17 | 3-[3-((1,3-dioxolan-2-yl)propyl]-2-phenyl-benzimidazolium perchlorate |
| QAS-18 | 5-chloro-3-(2-formylethyl)-2-methylbenzothiazolium bromide |
| QAS-19 | 3-(3,3-di(ethylthio)propyl]-2-methylbenzothiazolium iodide |
| QAS-20 | 3-(6,6-diethoxy-n-hexyl)-2-methylnaphtho-[2,1-d]thiazolium bromide |
| QAS-21 | 3-[2-(1,3-dithiolan-2-yl)ethyl]-2-methylbenzothiazolium iodide |
| QAS-22 | 3-(3,3-diethoxypropyl)-2-ethylthionaphtho-[2,3-d]thiazolium methylsulfate |
| QAS-23 | 3-[3-(1,3-dioxolan-2-yl)propyl]-1-ethyl-2-phenyl-benzimidazolium perchlorate |

In addition, N-substituted quaternary ammonium salts of the type disclosed in Adachi et al U.S. Pat. No. 4,115,122 can be employed. It is also specifically contemplated to employ the 3,3-disubstituted acylhydrazinophenylthiourea nucleating agents of this patent application in combination with the monosubstituted acylhydrazinophenylthiourea nucleating agents of Leone et al U.S. Pat. No. 4,030,925, cited above, and N-(acylhydrazinophenyl)thioamides of Leone et al U.S. Pat. No. 4,080,207, both here incorporated by reference. It is further recognized that adducts of a thioamine and glutaraldehyde or acrylic aldehyde, such as those described in Plakunov et al U.S. Pat. No. 3,708,302 and Amering U.S. Pat. No. 3,869,286, are capable of acting as nucleating gents and are useful in combination with the nucleating agents of this invention. Still other useful nucleating agents are disclosed in U.K. Pat. Nos. 2,011,391 and 2,012,443.

The silver halide emulsions can be spectrally sensitized with cyanine, merocyanine, and other polymethine dyes and supersensitizing combinations thereof well known in the art. Spectral sensitizers in conventional surface-sensitive emulsions are comparably effective in the emulsions of this invention. In general, they enhance nucleation. Nonionic, zwitterionic and anionic spectral sensitizers are preferred. Particularly effective are carboxy-substituted merocyanine dyes of the thiohydantoin type described by Stauffer et al U.S. Pat. No. 2,490,758.

Effective red sensitizers are the carbocyanines of formula (V)

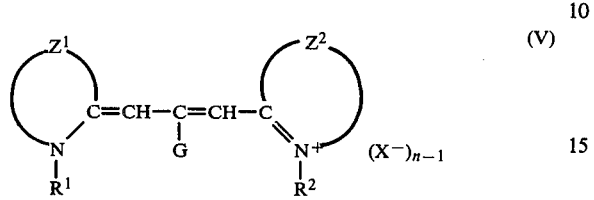

wherein
- each of $Z^1$ and $Z^2$ represents the atoms necessary to form a benzothiazole, benzoselenazole, naphthothiazole, or naphthoselenazole, the benzothiazole and benzoselenazole being preferably 5- and/or 6-substituted with groups such as lower alkyl, lower alkoxy, chloro, bromo, fluoro, hydroxy, acylamino, cyano, and trifluoromethyl,
- G represents hydrogen and lower alkyl, preferably ethyl or methyl,
- each of $R^1$ and $R^2$ represents lower alkyl or hydroxy(lower)alkyl, at least one of $R^1$ and $R^2$ being preferably acid-substituted(lower)alkyl, such as, carboxyethyl, sulfopropyl, and sulfatoethyl,
- X represents an acid anion, and
- n is 1 or 2.

Particularly effective are certain supersensitizing combinations of the above dyes with each other and with dyes or other adsorbed organic compounds having polarographic oxidation potentials ($E_{ox}$) of about 0.3 to 0.9 volt. Many such combinations are described in Mees U.S. Pat. No. 2,075,048, Carroll et al U.S. Pat. Nos. 2,313,922, 2,533,426, 2,688,545, and 2,704,714, Jones U.S. Pat. No. 2,704,717, and Schwan U.S. Pat. No. 3,672,898, and include, as well, the acid-substituted analogues thereof well known in the art.

Effective green sensitizers are carbocyanines and cyanines of formulas (VI) and (VII)

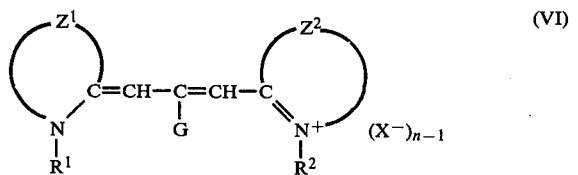

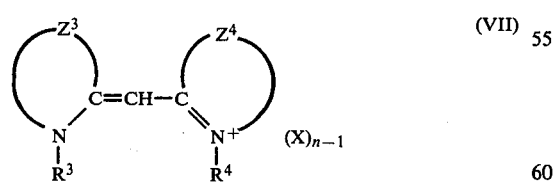

wherein
- each of $Z^1$ and $Z^2$ represents the atoms necessary to form benzoxazole and benzimidazole nuclei, benzimidazole being substituted in the 3-position by lower alkyl or aryl, and preferably in the 5- and/or 6-positions with groups selected from fluoro, chloro, bromo, lower alkyl, cyano, acylamino and trifluoromethyl, and the benzoxazole ring preferably substituted in the 5- or 6-positions with lower alkyl, lower alkoxy, phenyl, fluoro, chloro, and bromo,
- $Z^3$ represents the atoms necessary to form benzothiazole, benzoselenazole, naphthothiazole, naphthoselenazole, or 2-quinoline,
- $Z^4$ represents the atoms necessary to form 2-quinoline,
- G represents lower alkyl and, if at least one of $Z^1$ and $Z^2$ forms benzimidazole, hydrogen,
- each of $R^1$, $R^2$, $R^3$ and $R^4$ represents lower alkyl or hydroxy(lower)alkyl, at least one of $R^1$ and $R^2$ and of $R^3$ and $R^4$ being preferably acid-substituted(lower)alkyl, such as, carboxyethyl, sulfopropyl, and sulfatoethyl,
- X represents an acid anion, and
- n is 1 or 2.

Particularly effective are certain supersensitizing combinations of the above dyes, such as those described in Carroll et al U.S. Pat. Nos. 2,688,545 and 2,701,198, Nys et al U.S. Pat. No. 2,973,264, and Schwan et al U.S. Pat. No. 3,397,060, and their acid-substituted analogues well known in the art.

Effective blue sensitizers are simple cyanines and merocyanines of formulas (VIII) and (IX)

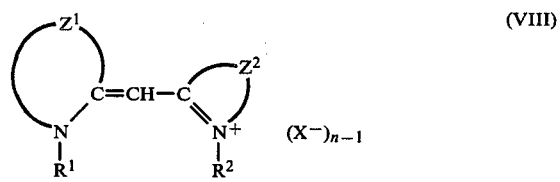

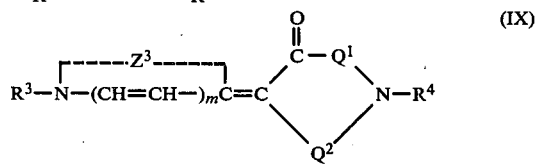

wherein
- each of $Z^1$ and $Z^2$ represents the atoms necessary to form benzothiazole, benzoselenazole, naphthothiazole and naphthoselenazole nuclei which may be substituted with groups, such as, chloro, methyl or methoxy, chloro, bromo, lower alkyl, or lower alkoxy,
- $Z^3$ represents benzothiazole, benzoselenazole which may be substituted as in $Z^1$ and $Z^2$, and a pyridine nucleus,
- $Q^1$ and $Q^2$ together represent the atoms necessary to complete a rhodanine, 2-thio-2,4-oxazolidinedione or 2-thiohydantoin ring, the latter having a second nitrogen atom with a substituent $R^5$,
- m represents 0 or 1,
- each of $R^1$, $R^2$ and $R^3$ represents lower alkyl or hydroxy(lower)alkyl, at least one of $R^1$ and $R^2$ being preferably acid-substituted(lower)alkyl, such as, carboxyethyl, sulfopropyl, and sulfatoethyl,
- $R^4$ and $R^5$ represent lower alkyl and hydroxy(lower)alkyl, and $R^4$ additionally can represent carboxyalkyl and sulfoalkyl,
- X is an acid anion, and
- n is 1 or 2.

(Lower alkyl in each occurrence of Formulas V to IX includes from 1 to 5 carbon atoms.)

The photographic elements are preferably color photographic elements which form dye images through the selective destruction, formation or physical removal of dyes.

The photographic elements can produce dye images through the selective destruction of dyes or dye precursors, such as silver-dye-bleach processes, as illustrated by A. Meyer, *The Journal of Photographic Science*, Volume 13, 1965, pages 90 through 97. Bleachable azo, azoxy, xanthene, azine, phenylmethane, nitroso complex, indigo, quinone, nitro-substituted, phthalocyanine, and formazan dyes, as illustrated by Stauner et al U.S. Pat. No. 3,754,923, Piller et al U.S. Pat. No. 3,749,576, Yoshida et al U.S. Pat. No. 3,738,839, Froelich et al U.S. Pat. No. 3,716,368, Piller U.S. Pat. No. 3,655,388, Williams et al U.S. Pat. No. 3,642,482, Gilman U.S. Pat. No. 3,567,448, Loeffel U.S. Pat. No. 3,443,953, Anderau U.S. Pat. Nos. 3,443,952 and 3,211,556, Mory et al U.S. Pat. Nos. 3,202,511 and 3,178,291, and Anderau et al U.S. Pat. Nos. 3,178,285 and 3,178,290 as well as their hydrazo, diazonium, and tetrazolium precursors and leuco and shifted derivatives, as illustrated by U.K. Pat. Nos. 923,265, 999,996, and 1,042,300, Pelz et al U.S. Pat. No. 3,684,513, Watanabe et al U.S. Pat. No. 3,615,493, Wilson et al U.S. Pat. No. 3,503,741, Boes et al U.S. Pat. No. 3,340,059, Gompf et al U.S. Pat. No. 3,493,372, and Puschel et al U.S. Pat. No. 3,561,970 can be employed.

The photographic elements can produce dye images through the selective formation of dyes, such as by reacting (coupling) a color-developing agent (e.g., a primary aromatic amine) in its oxidized form with a dye-forming coupler. The dye-forming couplers can be incorporated in the photographic elements, as illustrated by Schneider et al, *Die Chemie*, Volume 57, 1944, page 113, Mannes et al U.S. Pat. No. 2,304,940, Martinez U.S. Pat. No. 2,269,158, Jelley et al U.S. Pat. No. 2,322,027, Frolich et al U.S. Pat. No. 2,376,679, Fierke et al U.S. Pat. No. 2,801,171, Smith U.S. Pat. No. 3,748,141, Tong U.S. Pat. No. 2,772,163, Thirtle et al U.S. Pat. No. 2,835,579, Sawdey et al U.S. Pat. No. 2,533,514, Peterson U.S. Pat. No. 2,353,754, Seidel U.S. Pat. No. 3,409,435, and Chen *Research Disclosure*, Volume 159, July 1977, Item 15930.

In one form, the dye-forming couplers are chosen to form subtractive primary (i.e., yellow, magenta, and cyan) image dyes and are nondiffusible, colorless couplers, such as two- and four-equivalent couplers of the open chain ketomethylene, pyrazolone, pyrazolotriazole, pyrazolobenzimidazole, phenol, and naphthol type hydrophobically ballasted for incorporation in high-boiling organic (coupler) solvents. Such couplers are illustrated by Salminen et al U.S. Pat. Nos. 2,423,730, 2,772,162, 2,895,826, 2,710,803, 2,407,207, 3,737,316, and 2,367,531, Loria et al U.S. Pat. Nos. 2,772,161, 2,600,788, 3,006,759, 3,214,437, and 3,253,924, McCrossen et al U.S. Pat. No. 2,875,057, Bush et al U.S. Pat. No. 2,908,573, Gledhill et al U.S. Pat. No. 3,034,892, Weissberger et al U.S. Pat. Nos. 2,474,293, 2,407,210, 3,062,653, 3,265,506, and 3,384,657, Porter et al U.S. Pat. No. 2,343,703, Greenhalgh et al U.S. Pat. No. 3,127,269, Feniak et al U.S. Pat. Nos. 2,865,748, 2,933,391, and 2,865,751, Bailey et al U.S. Pat. No. 3,725,067, Beavers et al U.S. Pat. No. 3,758,308, Lau U.S. Pat. No. 3,779,763, Fernandez U.S. Pat. No. 3,785,829, U.K. Pat. No. 969,921, U.K. Pat. No. 1,241,069, U.K. Pat. No. 1,011,940, Vanden Eynde et al U.S. Pat. No. 3,762,921, Beavers U.S. Pat. No. 2,983,608, Loria U.S. Pat. Nos. 3,311,476, 3,408,194, 3,458,315, 3,447,928, and 3,476,563, Cressman et al U.S. Pat. No. 3,419,390, Young U.S. Pat. No. 3,419,391, Lestina U.S. Pat. No. 3,519,429, U.K. Pat. No. 975,928, U.K. Pat. No. 1,111,554, Jaeken U.S. Pat. No. 3,222,176 and Canadian Pat. No. 726,651, Schulte et al U.K. Pat. No. 1,248,924, and Whitmore et al U.S. Pat. No. 3,227,550.

The photographic elements can incorporate alkali-soluble ballasted couplers, as illustrated by Froelich et al and Tong, cited above. The photographic elements can be adapted to form nondiffusible image dyes using dye-forming couplers in developers, as illustrated by U.K. Pat. No. 478,984, Yager et al U.S. Pat. No. 3,113,864, Vittum et al U.S. Pat. Nos. 3,002,836, 2,271,238, and 2,362,598, Schwan et al U.S. Pat. No. 2,950,970, Carroll et al U.S. Pat. No. 2,592,243, Porter et al U.S. Pat. Nos. 2,343,703, 2,376,380, and 2,369,489, Spath U.K. Pat. No. 886,723 and U.S. Pat. No. 2,899,306, Tuite U.S. Pat. No. 3,152,896, and Mannes et al U.S. Pat. Nos. 2,115,394, 2,252,718, and 2,108,602.

The dye-forming couplers upon coupling can release photograhically useful fragments, such as development inhibitors or accelerators, bleach accelerators, developing agents, silver halide solvents, toners, hardeners, fogging agents, antifoggants, competing couplers, chemical or spectral sensitizers, and desensitizers. Development inhibitor-releasing (DIR) couplers are illustrated by Whitmore et al U.S. Pat. No. 3,148,062, Barr et al U.S. Pat. No. 3,227,554, Barr U.S. Pat. No. 3,733,201, Sawdey U.S. Pat. No. 3,617,291, Groet et al U.S. Pat. No. 3,703,375, Abbott et al U.S. Pat. No. 3,615,506, Weissberger et al U.S. Pat. No. 3,265,506, Seymour U.S. Pat. No. 3,620,745, Marx et al U.S. Pat. No. 3,632,345, Mader et al U.S. Pat. No. 3,869,291, U.K. Pat. No. 1,201,110, Oishi et al U.S. Pat. No. 3,642,485, Verbrugghe U.K. Pat. No. 1,236,767, Fujiwhara et al U.S. Pat. No. 3,770,436, and Matsuo et al U.S. Pat. No. 3,808,945. DIR compounds which do not form dye upon reaction with oxidized color-developing agents can be employed, as illustrated by Fujiwhara et al German OLS No. 2,529,350 and U.S. Pat. Nos. 3,928,041, 3,958,993, and 3,961,959, Odenwalder et al German OLS No. 2,448,063, Tanaka et al German OLS No. 2,610,546, Kikuchi et al U.S. Pat. No. 4,049,455, and Credner et al U.S. Pat. No. 4,052,213. DIR compounds which oxidatively cleave can be employed, as illustrated by Porter et al U.S. Pat. No. 3,379,529, Green et al U.S. Pat. No. 3,043,690, Barr U.S. Pat. No. 3,364,022, Duennebier et al U.S. Pat. No. 3,297,445, and Rees et al U.S. Pat. No. 3,287,129.

The photographic elements can incorporate colored dye-forming couplers, such as those employed to form integral masks for negative color images, as illustrated by Hanson U.S. Pat. No. 2,449,966, Glass et al U.S. Pat. No. 2,521,908, Gledhill et al U.S. Pat. No. 3,034,892, Loria U.S. Pat. No. 3,476,563, Lestina U.S. Pat. No. 3,519,429, Friedman U.S. Pat. No. 2,543,691, Puschel et al U.S. Pat. No. 3,028,238, Menzel et al U.S. Pat. No. 3,061,432, and Greenhalgh U.K. Pat. No. 1,035,959, and/or competing couplers, as illustrated by Murin et al U.S. Pat. No. 3,876,428, Sakamoto et al U.S. Pat. No. 3,580,722, Puschel U.S. Pat. No. 2,998,314, Whitmore U.S. Pat. No. 2,808,329, Salminen U.S. Pat. No. 2,742,832, and Weller et al U.S. Pat. No. 2,689,793.

The photographic elements can produce dye images through the selective removal of dyes. Negative or positive dye images can be produced by the immobilization of incorporated color-providing substances as a function of exposure and development, as illustrated by U.K. Pat. Nos. 1,456,413, 1,479,739, 1,475,265, and 1,471,752, Friedman U.S. Pat. No. 2,543,691, Whitmore U.S. Pat. No. 3,227,552, Bloom et al U.S. Pat. No. 3,443,940, Morse U.S. Pat. No. 3,549,364, Cook U.S. Pat. No. 3,620,730, Danhauser U.S. Pat. No. 3,730,718, Staples U.S. Pat. No. 3,923,510, Oishi et al U.S. Pat. No. 4,052,214, and Fleckenstein et al U.S. Pat. No. 4,076,529.

The photographic elements can contain antistain agents (i.e., oxidized developing agent scavengers) to prevent developing agents oxidized in one dye image layer unit from migrating to an adjacent dye image layer unit. Such antistain agents include ballasted or otherwise nondiffusing antioxidants, as illustrated by Weissberger et al U.S. Pat. No. 2,336,327, Loria et al U.S. Pat. No. 2,728,659, Vittum et al U.S. Pat. No. 2,360,290, Jelley et al U.S. Pat. No. 2,403,721, and Thirtle et al U.S. Pat. No. 2,701,197. To avoid autooxidation the antistain agents can be employed in combination with other antioxidants, as illustrated by Knechel et al U.S. Pat. No. 3,700,453.

The photographic elements can include image dye stabilizers. Such image dye stabilizers are illustrated by U.K. Pat. No. 1,326,889, Lestina et al U.S. Pat. Nos. 3,432,300 and 3,698,909, Stern et al U.S. Pat. No. 3,574,627, Brannock et al U.S. Pat. No. 3,573,050, Arai et al U.S. Pat. No. 3,764,337, and Smith et al U.S. Pat. No. 4,042,394.

This invention is particularly useful with photographic elements used in image transfer processes or in image transfer film units.

Image transfer systems include colloid transfer systems, as illustrated by Yutzy et al U.S. Pat. Nos. 2,596,756 and 2,716,059, silver salt diffusion transfer systems, as illustrated by Rott U.S. Pat. No. 2,352,014, Land U.S. Pat. No. 2,543,181, Yackel et al U.S. Pat. No. 3,020,155, and Land U.S. Pat. No. 2,861,885, imbibition transfer systems, as illustrated by Minsk U.S. Pat. No. 2,882,156, and color image transfer systems, as illustrated by *Research Disclosure*, Volume 151, November 1976, Item 15162, and Volume 123, July 1974, Item 12331.

Color image transfer systems (including emulsion layers, receiving layers, timing layers, acid layers, processing compositions, supports, and cover sheets) and the images they produce can be varied by choosing among a variety of features, combinations of which can be used together as desired.

Film units can be chosen which are either integrally laminated or separated during exposure, processing and/or viewing, as illustrated by Rogers U.S. Pat. No. 2,983,606, Beavers et al U.S. Pat.No. 3,445,228, Whitmore, Canadian Pat. No. 674,082, Friedman et al U.S. Pat. No. 3,309,201, Land U.S. Pat. Nos. 2,543,181, 3,053,659, 3,415,644, 3,415,645, and 3,415,646, and Barr et al U.K. Pat. No. 1,330,524.

A variety of approaches are known in the art for obtaining transferred dye images. The approaches can be generally categorized in terms of the initial mobility of dye or dye precursor. (Initial mobility refers to the mobility of the dye or dye precursor when it is contacted by the processing solution. Initially mobile dyes and dye precursors as coated do not migrate prior to contact with processing solution.)

Dye image-providing compounds are classified as either positive-working or negative-working. Positive-working dye image-providing compounds are those which produce a positive transferred dye image when employed in combination with a conventional, negative-working silver halide emulsion. Negative-working dye image-providing compounds are those which produce a negative transferred dye image when employed in combination with conventional, negative-working silver halide emulsions. (The foregoing techniques, such as those referred to in *Research Disclosure*, Vol. 176, December 1978, Item 17643, paragraph XXIII-E.) When, as in the present invention, the silver halide emulsions are direct-positive emulsions, positive-working dye image-providing compounds produce negative transferred dye images and negative-working dye image-providing compounds produce positive transferred dye images.

Image transfer systems, which include both the dye image-providing compounds and the silver halide emulsions, are positive-working when the transferred dye image is positive and negative-working when the transferred dye image is negative. When a retained dye image is formed, it is opposite in sense to the transferred dye image.

A variety of dye image transfer systems have been developed and can be employed in the practice of this invention. One approach is to employ ballasted dye-forming (chromogenic) or nondye-forming (nonchromogenic) couplers having a mobile dye attached at a coupling-off site. Upon coupling with an oxidized color developing agent, such as a para-phenylenediamine, the mobile dye is displaced so that it can transfer to a receiver. This negative-working image transfer approach is illustrated by Whitmore et al U.S. Pat. No. 3,227,550, Whitmore U.S. Pat. No. 3,227,552, and Fujihara et al U.K. Pat. No. 1,445,797, the disclosures of which are here incorporated by reference.

In a preferred image transfer system according to this invention employing negative-working dye image-providing compounds, a cross-oxidizing developing agent (electron transfer agent) develops silver halide and then cross-oxidizes with a compound containing a dye linked through an oxidizable sulfonamido group, such as a sulfonamidophenol, sulfonamidoaniline, sulfonamidoanilide, sulfonamidopyrazolobenzimidazole, sulfonamidoindole or sulfonamidopyrazole. Following cross-oxidation, hydrolytic deamidation cleaves the mobile dye with the sulfonamido group attached. Such systems are illustrated by Fleckenstein U.S. Pat. Nos. 3,928,312 and 4,053,312, Fleckenstein U.S. Pat. No. 4,076,529, Melzer et al U.K. Pat. No. 1,489,694, Deguchi German OLS No. 2,729,820, Koyama et al German OLS No. 2,613,005, Vetter et al German OLS No. 2,505,248, and Kestner et al *Research Disclosure*, Volume 151, November 1976, Item 15157. Also specifically contemplated are otherwise similar systems which employ an immobile, dye-releasing (a) hydroquinone, as illustrated by Gompf et al U.S. Pat. No. 3,698,897 and Anderson et al U.S. Pat. No. 3,725,062, (b) para-phenylenediamine, as illustrated by Whitmore et al Canadian Pat. No. 602,607, or (c) quaternary ammonium compound, as illustrated by Becker et al U.S. Pat. No. 3,728,113.

Another specifically contemplated dye image transfer system which is negative-working reacts an oxidized electron transfer agent or, specifically, in certain forms, an oxidized para-phenylenediamine with a ballasted phenolic coupler having a dye attached through a sulfonamido linkage. Ring closure to form a phenazine releases mobile dye. Such an imaging approach is illustrated by Bloom et al U.S. Pat. Nos. 3,443,939 and 3,443,940.

In still another negative-working system, ballasted sulfonylamidrazones, sulfonylhydrazones or sulfonylcarbonylhydrazides can be reacted with oxidized para-phenylenediamine to release a mobile dye to be transferred, as illustrated by Puschel et al U.S. Pat. Nos. 3,628,952 and 3,844,785. In an additional negative-working system, a hydrazide can be reacted with silver halide having a developable latent image site and thereafter decompose to release a mobile, transferable dye, as illustrated by Rogers U.S. Pat. No. 3,245,789, Kohara et al, *Bulletin Chemical Society of Japan,* Volume 43, pages 2433 through 2437, and Lestina et al *Research Disclosure,* Volume 28, December 1974, Item 12832.

Image transfer systems employing negative-working image dye-providing compounds are also known in which dyes are not initially present, but are formed by reactions occurring in the photographic element or receiver following exposure. For example, a ballasted coupler can react with color developing agent to form a mobile dye, as illustrated by Whitmore et al U.S. Pat. No. 3,227,550, Whitmore U.S. Pat. No. 3,227,552, Bush et al U.S. Pat. No. 3,791,827, and Viro et al U.S. Pat. No. 4,036,643. An immobile compound containing a coupler can react with oxidized para-phenylenediamine to release a mobile coupler which can react with additional oxidized para-phenylenediamine before, during or after release to form a mobile dye, as illustrated by Figueras et al U.S. Pat. No. 3,734,726 and Janssens et al German OLS No. 2,317,134. In another form, a ballasted amidrazone reacts with an electron transfer agent as a function of silver halide development to release a mobile amidrazone which reacts with a coupler to form a dye at the receiver, as illustrated by Ohyama et al U.S. Pat. No. 3,933,493.

An image to be viewed can be transferred from the image-forming layers. A retained image can be formed for viewing as a concurrently formed complement of the transferred image. Positive transferred images and useful negative retained images can be formed with the direct positive silver halide emulsions of this invention when imaging chemistry is negative-working. Images retained in and transferred from the image-forming layers are illustrated by U.K. Pat. No. 1,456,413, Friedman U.S. Pat. No. 2,543,691, Bloom et al U.S. Pat. No. 3,443,940, Staples U.S. Pat. No. 3,923,510, and Fleckenstein et al U.S. Pat. No. 4,076,529.

Where mobile dyes are transferred to the receiver a mordant is commonly present in a image dye-providing layer. Mordants and mordant containing layers are described in the following references which are incorporated by reference: Sprague et al U.S. Pat. No. 2,548,564, Weyerts U.S. Pat. No. 2,548,575, Carroll et al U.S. Pat. No. 2,675,316, Yutzy et al U.S. Pat. No. 2,713,305, Saunders et al U.S. Pat. No. 2,756,149, Reynolds et al U.S. Pat. No. 2,768,078, Gray et al U.S. Pat. No. 2,839,401, Minsk U.S. Pat. Nos. 2,882,156 and 2,945,006, Whitmore et al U.S. Pat. No. 2,940,849, Condax U.S. Pat. No. 2,952,566, Mader et al U.S. Pat. No. 3,016,306, Minsk et al U.S. Pat. Nos. 3,048,487 and 3,184,309, Bush U.S. Pat. No. 3,271,147, Whitmore U.S. Pat. No. 3,271,148, Jones et al U.S. Pat. No. 3,282,699, Wolf et al U.S. Pat. No. 3,408,193, Cohen et al U.S. Pat. Nos. 3,488,706, 3,557,066, 3,625,694, 3,709,690, 3,758,445, 3,788,855, 3,898,088, and 3,944,424, Cohen U.S. Pat. No. 3,639,357, Taylor U.S. Pat. No. 3,770,439, Campbell et al U.S. Pat. Nos. 3,958,995 and 4,193,795; and Ponticello et al *Research Disclosure,* Vol. 120, April 1974, Item 12045.

One-step processing can be employed, as illustrated by U.K. Pat. No. 1,471,752, Land U.S. Pat. No. 2,543,181, Rogers U.S. Pat. No. 2,983,606 (pod processing), Land U.S. Pat. No. 3,485,628 (soak image-former and laminate to receiver) and Land U.S. Pat. No. 3,907,563 (soak receiver and laminate to image-forming element) or multi-step processing can be employed, as illustrated by Yutzy U.S. Pat. No. 2,756,142, Whitmore et al U.S. Pat. No. 3,227,550, and Faul et al U.S. Pat. No. 3,998,637.

Preformed reflective layers can be employed, as illustrated by Whitmore Canadian Pat. No. 674,082, Beavers U.S. Pat. No. 3,445,228, Land U.S. Pat. Nos. 2,543,181, 3,415,644, '645 and '646, and Barr et al U.K. Pat. No. 1,330,524 or processing-formed reflective layers can be employed, as illustrated by Land U.S. Pat. Nos. 2,607,685 and 3,647,437, Rogers U.S. Pat. No. 2,983,606, Buckler U.S. Pat. No. 3,661,585.

Generally, the image transfer film units in accordance with this invention comprise:

(1) a photographic element comprising a support having thereon at least one silver halide emulsion layer containing radiation-sensitive internal latent image silver halide grains and a 3,3-disubstituted arylhydrazinophenylthiourea nucleating agent, the emulsion layer preferably having in contact therewith an image dye-providing material, (2) an image-receiving layer, which can be located on a separate support and superposed or adapated to be superposed on the photographic element or, preferably, can be coated as a layer in the photographic element, (3) an alkaline processing composition, (4) means containing and adapted to release the alkaline processing composition into contact with the emulsion layer, and (5) a silver halide developing agent located in at least one of the photographic element and alkaline processing composition so that the processing composition and developing agent, when brought together, form a silver halide surface developer.

In highly preferred embodiments, the film units of this invention contain a support having thereon a layer containing a blue-sensitive emulsion and in contact therewith a yellow image dye-providing material, a red-sensitive silver halide emulsion and in contact therewith a cyan image dye-providing material, and a green-sensitive emulsion and in contact therewith a magenta image dye-providing material, and preferably all of said image dye-providing materials are initially immobile dye-providing materials.

The terms "diffusible" (or "mobile") and "immobile" (or "nondiffusible"), as used herein, refer to compounds which are incorporated in the photographic element and, upon contact with an alkaline processing solution, are substantially diffusible or substantially immobile, respectively, in the hydrophilic colloid layers of a photographic element.

The term "image dye-providing material", as used herein, is understood to refer to those compounds which are employed to form dye images in photographic elements. These compounds include dye developers, shifted dyes, color couplers, oxichromic compounds, dye redox releasers, etc, as described above in connection with positive-working and negative-working image transfer systems.

In one preferred embodiment, the receiver layer is coated on the same support with the photosensitive silver halide emulsion layers, the support is preferably a transparent support, an opaque layer is preferably positioned between the image-receiving layer and the photosensitive silver halide layer, and the alkaline processing composition preferably contains an opacifying substance, such as carbon or a pH-indicator dye which is discharged into the film unit between a dimensionally stable support or cover sheet and the photosensitive element.

In certain embodiments, the cover sheet can be superposed or is adapted to be superposed on the photosensitive element. The image-receiving layer can be located on the cover sheet so that it becomes an image-receiving element. In certain preferred embodiments where the image-receiving layer is located in the photosensitive element, a neutralizing layer is located on the cover sheet.

Increases in maximum density can be obtained in color image transfer film units containing internally sulfur and gold-sensitized emulsions of the type described by Evans U.S. Pat. No. 3,761,276, and sulfonamidonaphthol redox dye-releasing compounds of the type described by Fleckenstein British Pat. No. 1,405,662, by incorporation into the emulsion layers of a variety of chemical addenda generally recognized in the art as antifoggants or development inhibitors, as well as hydrolyzable precursors thereof. Many of these compounds also provide improved stabilization of sensitometric properties of liquid emulsion and of the storage life of the coated emulsion. The effects, shown in film units of the type described in Examples 40 through 42 of British Pat. No. 1,405,662, are in addition to the effect of 5-methylbenzotriazole in the processing composition even when the latter is present in quantities as high as 4 grams per liter. Effective compounds in general are selected from the group consisting of (a) 1,2,3-triazoles, tetrazoles and benzotriazoles having an N—$R^1$ group in the heterocyclic ring, wherein $R^1$ represents hydrogen or an alkali-hydrolyzable group, or (b) heterocyclic mercaptans or thiones and precursors thereof, mostly having one of the formulas (X) or (XI):

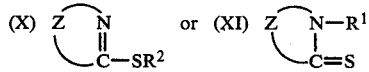

wherein

Z comprises the atoms necessary to complete an azole ring, and $R^2$ represents, in addition to the groups specified above for $R^1$, a metal ion.

The compounds are generally employed at concentrations less than about 300 mg per mole of silver, each compound having an optimum concentration above which development and/or nucleation are inhibited and $D_{max}$ decreases with increasing concentration. Specifically preferred antifoggants and stabilizers, as well as other preferred color image transfer film unit and system features, are more specifically disclosed in *Research Disclosure*, Volume 151, November 1976, Item 15162, the disclosure of which is hereby incorporated by reference.

A more detailed description of useful image transfer film units and systems is contained in the patents relating to image transfer cited above, the disclosures of which are here incorporated by reference. A specific, preferred image-transfer film unit and image transfer system is that disclosed by Leone et al U.S. Pat. No. 4,030,925, cited above, and here incorporated by reference.

The following examples illustrate the invention. All temperatures are in °C. Unless otherwise indicated, parenthetically indicated coating coverages are in grams per square meter.

EXAMPLE 1

Preparation of
1-[4-(2-formylhydrazino)phenyl]-3,3-dimethylthiourea
(NA-1)

1-Formyl-2-(4-aminophenyl)hydrazine (1.51 g, 0.01 mole) and triethylamine (1.0 g, 0.01 mole) were mixed with dry acetonitrile (30 ml). The mixture was kept under a nitrogen atmosphere and a solution of dimethylthiocarbamoyl chloride (1.24 g, 0.01 mole) in acetonitrile (10 ml) was added dropwise at room temperature. After the addition was complete, the reaction mixture was chilled in ice, then filtered. The solid was washed with ethanol and allowed to dry. The material was stirred in water (40 ml) and heated to 60° C. to remove any hydrochloride salts. The aqueous mixture was filtered; the solid was washed with ether and dried. This gave 0.60 g (25 percent) of product as a pale tan powder, m.p. 187°–189° C.

EXAMPLE 2

Preparation of
1-[4-(2-acetylhydrazino)phenyl]-3,3-dimethylthiourea
(NA-5)

The procedure for the preparation of NA-1 in Example 1 was followed with 1-acetyl-2-(4-aminophenyl)hydrazine (0.82 g, 0.005 mole), dimethylthiocarbamoyl chloride (0.62 g, 0.005 mole) and N,N-diisopropylethylamine (0.65 g, 0.005 mole). Yield 0.30 g (24 percent), m.p. 187°–189° C.

EXAMPLE 3

Preparation of
1-[4-(2-formylhydrazino)phenyl]-3,3-dibenzylthiourea
(NA-11)

4-(2-Formylhydrazino)phenyl isothiocyanate was first prepared in the following manner: 1-formyl-2-(4-aminophenyl)hydrazine (1.1 g, 0.0075 mole) was dissolved in dry acetone (75 ml) and the resulting solution was cooled to −78° C. in a dry ice-acetone bath. The reaction mixture was stirred and kept under a nitrogen atmosphere. A solution of 1,1'-thiocarbonyldiimidazole (1.35 g, 0.0075 mole) in dry acetone (75 ml) was added dropwise to the reaction mixture. After the addition was complete, the mixture was stirred for 30 minutes at −78° C., then allowed to warm to room temperature. The solvent was removed at reduced pressure. The remaining solid residue was stirred in water at room temperature. The solid was filtered off, washed with water, then ether, and allowed to dry. The crude product was recrystallized from acetone to give 0.80 g (55 percent) of a white crystalline powder, m.p. 178°–180° C.

Dibenzylamine (0.20 g, 0.001 mole) and 4-(2-formylhydrazino)phenyl isothiocyanate (0.19 g, 0.001 mole) were mixed in ethanol (25 ml) and the resulting mixture was heated to reflux for 20 minutes. The reaction mixture was cooled to room temperature, then was chilled in ice. After scratching the flask walls, a white crystalline solid was separated out of solution. The solid was filtered off, washed thoroughly with ether, and allowed to dry. This gave 0.31 g (80 percent) of product as a white crystalline powder, m.p. 174°–176° C.

EXAMPLE 4

Preparation of 1-[4-(2-acetylhydrazino)phenyl]-3,3-dibenzylthiourea (NA-12)

4-(2-Acetylhydrazino)phenyl isothiocyanate was prepared as described for NA-11 in Example 4 with 1-acetyl-2-(4-aminophenyl)hydrazine (1.23 g, 0.0075 mole) and 1,1'-thiocarbonyldiimidazole (1.35 g, 0.0075 mole). Yield 1.20 g (77 percent), m.p. 172°–174° C.

Dibenzylamine (0.20 g, 0.001 mole) and 4-(2-acetylhydrazino)phenyl isothiocyanate (0.21 g, 0.001 mole) were reacted according to the procedure described for NA-11 in Example 3. Yield 0.35 g (88 percent), m.p. 207°–209° C.

EXAMPLE 5

Preparation of 1-[4-(2-formylhydrazino)phenyl]-3-methyl-3-phenylthiourea (NA-14)

N-Methylaniline (0.11 g, 0.001 mole) and 4-(2-formylhydrazino)phenyl isothiocyanate (0.19 g, 0.001 mole) were reacted according to the procedure described for NA-11 in Example 3. Yield 0.15 g (50 percent), m.p. 137°–139° C.

EXAMPLE 6

Preparation of 1-[4-(2-formylhydrazino)phenyl]-3,3-dibutylthiourea (NA-15)

Di-n-butylamine (0.13 g, 0.001 mole) and 4-(2-formylhydrazino)phenyl isothiocyanate (0.19 g, 0.001 mole) were reacted according to the procedure described for NA-11 in Example 3. Yield 0.10 g (31 percent), m.p. 139°–141° C.

EXAMPLE 7

Preparation of 4-[4-(2-formylhydrazino)phenylthiocarbamoyl]morpholine (NA-21)

Morpholine (0.087 g, 0.001 mole) and 4-(2-formylhydrazino)phenyl isothiocyanate (0.19 g, 0.001 mole) were reacted according to the procedure described for NA-11 in Example 3. Yield 0.22 g (79 percent), m.p. 204°–206° C.

EXAMPLE 8

Preparation of 1-[4-(2-formylhydrazino)phenylthiocarbamoyl]piperidine (NA-32)

Piperidine (0.085 g, 0.001 mole) and 1-(2-formylhydrazino)phenyl isothiocyanate (0.19 g, 0.001 mole) were reacted according to the procedure described for NA-11 in Example 3. Yield 0.14 g (50 percent), m.p. 174°–176° C.

EXAMPLE 9

Preparation of 1-[4-(2-formylhydrazino)phenylthiocarbamoyl]pyrrolidine (NA-26)

Pyrrolidine (0.071 g, 0.001 mole) and 1-(2-formylhydrazino)phenyl isothiocyanate (0.19 g, 0.001 mole) were reacted according to the procedure described for NA-11 in Example 3. Yield 0.15 g (58 percent), m.p. 199°–201° C.

EXAMPLE 10

Preparation of 1-[4-(2-formylhydrazino)phenylthiocarbamoyl]-3-pyrroline (NA-25)

3-Pyrroline (0.069 g, 0.001 mole) and 1-(2-formylhydrazino)phenyl isothiocyanate (0.19 g, 0.001 mole) were reacted according to the procedure described for NA-11 in Example 3. Yield 0.18 g (69 percent), m.p. 218°–220° C.

EXAMPLE 11

Photographic Comparisons

A photographic multicolor image transfer element was prepared by coating onto a polyester form support to produce the indicated layer arrangement. (Coverages are expressed in $g/m^2$ unless otherwise specified.)

---

Layer 9-Overcoat layer of gelatin (0.86) and a latex mordant, poly(styrene-co-N-vinylbenzyl-N-benzyl-N,N'-dimethylammonium sulfate-co-divinylbenzene (0.11)

Layer 8 Blue-sensitive internal image gelatin (0.81) silver bromide (0.75) emulsion; sodium 5-octadecylhydroquinoe-2-sulfonate (12 g/mole Ag); and the same prior art nucleating agent present in Layer 2 (10 mg/mole Ag)

Layer 7-Gelatin (1.08) and a yellow redox dye-releaser of the type described in U.S. Pat. No. 4,013,633 (0.65)

Layer 6-Interlayer of gelatin (0.97) and di-dodecylhydroquinone (0.70)

Layer 5-Green-sensitive internal image gelatin(0.81) silver bromide (0.75) emulsion; sodium 5-octadecylhydroquinone-2-sulfonate (12 g/mole Ag); and the same prior art nucleating agent present in Layer 2 (10 mg/mole Ag)

Layer 4-Gelatin (1.08) and a magenta redox dye-releaser of the type described in U.S. Pat. No. 3,954,476 (0.54)

Layer 3-Interlayer of gelatin (0.97) and di-dodecylhydroquinone (0.70)

Layer 2-Red-sensitive internal image gelatin (1.08) silver bromide (0.75) emulsion; sodium 5-octadecylhydroquinone-2-sulfonate (12 g/mole Ag); and prior art nucleating agent 1-[4-(2-formylhydrazino)phenyl]-3-methylthiourea (C-1) (8 mg/mole Ag)

Layer 1-Gelatin (1.08) and a cyan redox dye-releaser of the type disclosed in U.S. Pat. No. 3,942,987 (0.54)

SUPPORT

---

A second element was identically prepared, except that the three emulsion layers each contained the nucleating agent 1-[4-(2-formylhydrazino)phenyl]-3,3-dimethylthiourea (NA-1) of the invention substituted at the same concentration for the prior art nucleating agent 1-[4-(2-formylhydrazino)phenyl]-3-methylthiourea (C-1).

Each element was exposed to a multicolor graduated density test object for 0.5 second and soaked for 15 seconds in an activator at 29° C., identified as Activator Solution A (described below in Table IV).

TABLE IV

| benzyl alcohol | 10 ml |
|---|---|
| 5-methylbenzotriazole | 1 g |
| 11-aminoundecanoic acid | 2 g |
| 6-aminohexanoic acid | 10 g |
| 0.5 N potassium hydroxide to pH 13.5 | 1 liter |

The element was then laminated to a dry image receiver sheet for two minutes, then peeled apart, and the receiver was washed with water.

The receiver sheet comprised the following layers coated on a polyolefin-coated paper support.

Layer 2-An overcoat layer or polyvinyl alcohol (0.11) (Elvanol 71-30)
Layer 1-A mordant layer of gelatin (2.28) and a latex poly(styrene-co-N-vinylbenzyl-N-benzyl-N,N-dimethylammonium sulfate-co-divinylbenzene) (2.28), 4-hydroxymethyl-4-methyl-1-phenyl-3-pyrazolidinone (0.16)
SUPPORT The $D_{max}$ and $D_{min}$ of the sensitometric curves are shown in Table V.

TABLE V

| | $D_{max}$ | | | $D_{min}$ | | |
|---|---|---|---|---|---|---|
| Nucleating Agent | Blue | Green | Red | Blue | Green | Red |
| 1-[4-(2-formylhydrazino)phenyl] 3-methylthiourea (C-1) | 1.88 | 2.15 | 0.35 | 0.25 | 0.34 | 0.19 |
| 1-[4-(2-formylhydrazino)phenyl]-3,3-dimethylthiourea NA-1) | 2.26 | 2.45 | 2.40 | 0.38 | 0.54 | 0.35 |

The data show that nucleating agent NA-1 is a more active nucleating agent than the 3-mono-substituted nucleating agent C-1 as indicated by the higher $D_{max}$ and $D_{min}$ values at the same concentration. An unexpected result of coating this layer structure directly on polyester support is overcoming the suppression of the release of cyan dye in layers containing the nucleating agent C-1. This suppression is completely overcome by using the 3,3-disubstituted thiourea-containing nucleating agents of this invention.

EXAMPLE 12

A series of photographic single color image transfer elements were prepared having the following layers coated on a black opaque polyester support. The coatings differed only in the type of nucleating agent in the emulsion layer. The prior art nucleating agent 1-[4-(2-formylhydrazino)phenyl]-3-phenylthiourea (C 2) of U.S. Pat. No. 4,030,925 was coated at $4.5 \times 10^{-5}$ mole/mole Ag. The compounds of the invention were substituted at the same concentration in otherwise identical elements. The elements exhibited the following layer arrangement.

Layer 3-An overcoat layer of gelatin (0.86) and a latex mordant poly(styrene-co-N-vinylbenzyl-N-benzyl-N,N-dimethylammonium sulfate-co-divinylbenzene) (0.11)
Layer 2-A green-sensitive internal-image silver bromide (0.43 Ag) gelatin (1.1) emulsion including 12 g/mole sodium 5-octadecylhydroquinone-2-sulfonate and the -continued nucleating agent
Layer 1-Gelatin (1.34) and magenta redox dye-releaser (0.48) of the type disclosed in Fernandez U.S. Pat. No. 4,135,929
SUPPORT The elements were exposed as described in Example 11, given a 10 second soak in an activator, either Activator Solution A (described above in Table IV) or Activator Solution B (described below in Table VI) at 29° C., and then laminated to a dry image receiver sheet for two minutes, peeled apart, and the receiver sheet washed with water.

TABLE VI

| benzyl alcohol | 8 m |
|---|---|
| 15-methylbenzotriazole | 1 g |
| 11-aminoundecanoic acid | 2 g |
| KBr | 4 g |
| 0.5 N potassium hydroxide to pH 13.5 | 1 liter |

The receiver sheet was comprised of a mordant layer coated on a polyolefin-coated paper support, as indicated below.

A mordant layer of gelatin (1.71) and poly(N-vinylimidazole-co-3-β-hydroxyethyl-1-vinylimidazolium chloride) (2.28), 4-hydroxymethyl-4-methyl-1-phenyl-3-pyrazolidininone (0.16)
SUPPORT The activity levels of the nucleating agents are compared in Table VII, which compares relative nucleating activity of compounds of this invention with prior art nucleating agent C-2. The activity rating value is based upon the concentration of nucleating agent that is required to match as closely as possible the characteristic curve (that is, similar $D_{max}$, contrast, speed and $D_{min}$) as prior art nucleating agent C-2. For example, with C-2 assigned an activity rating of 1.0, a nucleating agent with a rating of 2.0 is twice as active; i.e., only one-half the concentration of nucleating agent on a molar weight basis is required to give the same relative curve shape as compound C-2. Acylhydrazinophenylthioureas having a formyl acyl group are more active than otherwise comparable nucleating agents.

TABLE VII

Relative Nucleation Activity

| | | Activity Rating | |
|---|---|---|---|
| | Nucleating Agent | Solution A | Solution B |
| C-2 | 1-[4-(2-formylhydrazino)phenyl]-3-phenylthiourea | 1.0 | 1.0 |
| NA-1 | 1-[4-(2-formylhydrazino)phenyl]-3,3-dimethylthiourea | 3.33 | 2.12 |

TABLE VII-continued

Relative Nucleation Activity

| Nucleating Agent | | Activity Rating Solution A | Solution B |
|---|---|---|---|
| NA-11 | 1-[4-(2-formylhydrazino)phenyl]-3,3-dibenzylthiourea | 2.5 | 1.5 |
| NA-14 | 1-[4-(2-formylhydrazino)phenyl]-3-methyl-3-phenylthiourea | 6.33 | 4.25 |
| NA-21 | 4-[4-(2-formylhydrazino)phenylthiocarbamoyl]morpholine | 4.33 | 2.63 |
| NA-25 | 1-[4-(2-formylhydrazino)phenylthiocarbamoyl]-3-pyrroline | 3.17 | 1.88 |
| NA-26 | 1-[4-(2-formylhydrazino)phenylthiocarbamoyl]pyrrolidine | 5.67 | 3.5 |
| NA-32 | 1-[4-(2-formylhydrazino)phenylthiocarbamoyl]piperidine | 5.33 | 3.63 |

EXAMPLE 13

A comparison between nucleating agent C-1 at a concentration of $1.8 \times 10^4$ mole/mole Ag and a nucleating agent of the invention was made utilizing an activator solution having a pH of only 12.0.

Single color image transfer elements were prepared having the following layer arrangement coated on a black opaque polyester support.

Layer 3 - An overcoat layer of gelatin (0.86) and a latex mordant poly(styrene-co-N-vinylbenzyl-N-benzyl-N,N-dimethylammonium sulfate-co-divinylbenzene) (0.11)
Layer 2 - A green-sensitive internal image silver bromide (1.07 Ag) gelatin (1.61) emulsion including 12 g/mole sodium 5-octadecylhydroquinone-2-sulfonate and the nucleating agent
Layer 1 - Gelatin (1.61) and a magenta redox dye-releaser E (0.54) of the type disclosed by U.S. Pat. No. 3,954,476
SUPPORT The elements were exposed for 0.2 second through a graduated density test object, soaked for 40 seconds in Activator Solution C (described below in Table VIII) at 22° C., and then laminated to a dry image receiver sheet for 3 minutes, peeled apart and the receiver sheet washed with water.

TABLE VIII

| Activator Solution C | |
|---|---|
| K$_3$PO$_4$ | 60 g |
| benzyl alcohol | 10 ml |
| 5-methylbenzotriazole | 1 g |
| 11-aminoundecanoic acid | 2 g |
| distilled water to | 1 liter |
| pH 12.0 | |

The receiver sheet was comprised of a mordant layer coated over a gelatin layer (0.86) on a polyolefin-coated paper support. The mordant layer consisted of gelatin (2.28) and poly(styrene-co-N-vinylbenzyl-N-benzyl-N,N-dimethylammonium sulfate-co-divinylbenzene) (2.28) and 4-hydroxymethyl-4-methyl-1-phenyl-3-pyrazolidinone (0.22).

The results are set forth below in Table IX.

TABLE IX

Relative Nucleation Activity

| Nucleator | Activity Rating Solution C |
|---|---|
| 1-[4-(2-formylhydrazino)phenyl]-3-methylthiourea (C-1) | 1.0 |
| 1-[4-(2-formylhydrazino)phenyl]-3,3-dimethylthiourea (NA-1) | 2.1 |

This demonstrates the superior nucleation activity of the nucleating agents of this invention as compared with prior art acylhydrazinophenylthiourea nucleating agents at lower pH levels.

EXAMPLE 14

To provide a direct comparison of a mono-substituted acetyl hydrazide nucleating agent according to Leone et al U.S. Pat. No. 4,030,925 and an otherwise identical disubstituted acetyl hydrazide nucleating agent according to this invention, single color image transfer elements were prepared having the following layer arrangement coated on a black opaque polyester support.

Layer 3 - An overcoat layer of gelatin (1.29) containing didodecyl hydroquinone (0.23) and 1-Phenyl-2-pyrazolin-3-yl-N-methyl-[2-(N-methyltrifluoroacetamidomethyl)-4-p-toluene-sulfonamidophenyl]carbamate
Layer 2 - A green-sensitive internal image silverbromide (0.48) gelatin (1.29) emulsion including 6 g/Ag mole sodium 5-octadecylhydroquinone-2-sulfonate and $1.12 \times 10^{-4}$ mole/Ag mole of the nucleating agent
Layer 1 - Gelatin (1.29), a magenta redox dye-releaser (0.48) of the type disclosed in Fernandez U.S. Pat. No. 4,135,929 and sodium 5-octadecylhydro-quinone-2-sulfonate (0.05)
SUPPORT The elements were exposed for 0.5 second to a multicolor graduated density test object, soaked for 13 seconds at 29° C. in an activator solution similar to Activator Solution B (but with no benzyl alcohol), then laminated to a dry image receiver sheet for two minutes, peeled apart and the receiver sheet washed with water. The receiver sheet was of the type described in Research Disclosure, Vol. 185, September 1979, Item 18534.

The nucleating agents employed and a comparison of the maximum and minimum densities produced are set forth below in Table X.

TABLE X

| | Dye Densities | |
|---|---|---|
| | D$_{max}$ | D$_{min}$ |
| 1-[4-(2-acetylhydrazino)phenyl]-3-benzyl-thiourea (C-3) | 0.92 | 0.10 |
| 1-[4-(2-acetylhydrazino)phenyl]-3,3-dibenzyl-thiourea (NA-12) | 1.26 | 0.10 |

As is apparent from the table, the nucleating agent NA-12 according to the invention produces a substantially higher maximum transferred dye density than the control C-3 which is otherwise identical, except for being mono-substituted. In comparing nucleating agent activity levels, described above in Example 12, the nucleating agent NA-12 has an activity level twice that of the control C-3.

The invention has been described in detail with particular reference to preferred embodiments thereof, but it will be understood that variations and modifications can be effected within the spirit and scope of the invention.

What is claimed is:

1. A silver halide emulsion comprised of silver halide grains capable of forming an internal latent image and, adsorbed to the surface of said silver halide grains, a nucleating amount of a 3,3-disubstituted acylhydrazinophenylthiourea of the formula $$R-\underset{\underset{O}{\|}}{C}-\underset{H}{N}-\underset{H}{N}-R^1-\underset{H}{N}-\underset{\underset{S}{\|}}{C}-N\underset{R^3}{\overset{R^2}{<}}$$

wherein

R is hydrogen or an alkyl, cycloalkyl, haloalkyl, alkoxyalkyl or phenylalkyl substituent, $R^1$ is a phenylene or alkyl, halo-, or alkoxysubstituted phenylene group, and $R^2$ and $R^3$ are independently selected from among alkyl, haloalkyl, alkoxyalkyl, or phenylalkyl substituents having from 1 to 18 carbon atoms, a cycloalkyl substituent; a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur and selenium atoms, the alkyl moieties, except as otherwise noted, in each instance include from 1 to 6 carbon atoms and the cycloalkyl moieties have from 3 to 10 carbon atoms.

2. A silver halide emulsion according to claim 1 wherein said 3,3-disubstituted acylhydrazinophenylthiourea is of the formula $$R-\underset{\underset{O}{\|}}{C}-\underset{H}{N}-\underset{H}{N}-\underset{\phantom{x}}{\bigcirc}-\underset{H}{N}-\underset{\underset{S}{\|}}{C}-N\underset{R^3}{\overset{R^2}{<}}$$

wherein

R is hydrogen or methyl and $R^2$ and $R^3$ are independently selected from among alkyl and phenylalkyl substituents, wherein the alkyl moieties are in each instance from 1 to 6 carbon atoms, and a phenyl nucleus having a Hammett sigma value-derived electron-withdrawing characteristic less positive than +0.50, or $R^2$ and $R^3$ together form a saturated heterocyclic nucleus forming a 5- or 6-membered ring, wherein the ring atoms are chosen from the class consisting of nitrogen, carbon, oxygen, sulfur, and selenium atoms.

3. A silver halide emulsion according to claim 2 wherein said 3,3-disubstituted acylhydrazino-phenylthiourea is present in a concentration of from 0.1 to 500 mg per mole of silver.

4. A silver halide emulsion according to claims 1, 2 or 3 wherein said silver halide grains are predominantly silver bromide and contain metal dopants occluded therein, which grains when coated on a photographic support, exposed to a light intensity scale, and developed for 5 minutes at 25° C. in test surface developer provide (a) a density of less than 0.4 and (b) a density of at least 0.5 less than when this testing procedure is repeated modifying the test surface developer by the inclusion of 0.5 gram per liter of potassium iodide, the test surface developer being of the following composition:

| Water | 500.0 cc |
|---|---|
| N-methyl-p-aminophenol sulfate | 2.5 g |
| Sodium sulfite, desiccated | 30.0 g |
| Hydroquinone | 2.5 g |
| Sodium metaborate | 10.0 g |
| Potassium bromide | 0.5 g |
| Water to make | 1.0 liter. |

5. A photographic element comprised of a support bearing a silver halide emulsion layer comprising silver halide grains capable of forming an internal latent image and, adsorbed to the surface of said silver halide grains, a nucleating amount of a 3,3-disubstituted acylhydrazinophenylthiourea of the formula $$R-\underset{\underset{O}{\|}}{C}-\underset{H}{N}-\underset{H}{N}-R^1-\underset{H}{N}-\underset{\underset{S}{\|}}{C}-N\underset{R^3}{\overset{R^2}{<}}$$

wherein

R is hydrogen or an alkyl, cycloalkyl, haloalkyl, alkoxyalkyl, or phenylalkyl substituent, $R^1$ is a phenylene or alkyl, halo-, or alkoxysubstituted phenylene group, and $R^2$ and $R^3$ are independently selected from among alkyl, haloalkyl, alkoxyalkyl, or phenylalkyl substituents having from 1 to 18 carbon atoms, a cycloalkyl substituent, a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur, and selenium atoms, the alkyl moieties, except as otherwise noted, in each instance include from 1 to 6 carbon atoms and the cycloalkyl moieties have from 3 to 10 carbon atoms.

6. A photographic element according to claim 5 wherein the 3,3-disubstituted acylhydrazinophenylthiourea is of the formula $$R-\underset{\underset{O}{\|}}{C}-\underset{H}{N}-\underset{H}{N}-\underset{\phantom{x}}{\bigcirc}-\underset{H}{N}-\underset{\underset{S}{\|}}{C}-N\underset{R^3}{\overset{R^2}{<}}$$

wherein

R is hydrogen or methyl and $R^2$ and $R^3$ are independently selected from among alkyl and phenylalkyl substituents, wherein the alkyl moieties are in each instance from 1 to 6 carbon atoms, and a phenyl nucleus having a Hammett sigma value-derived electron-withdrawing characteristic less positive than +0.50, or $R^2$ and $R^3$ together form a saturated heterocyclic nucleus forming a 5- or 6-membered ring, wherein the ring atoms are chosen from the class consisting of nitrogen, carbon, oxygen, sulfur, and selenium atoms.

7. A photographic element according to claims 5 or 6 wherein said 3,3-disubstituted acylhydrazinophenylthiourea is present in a concentration of from 1.0 to 100 mg per mole of silver.

8. A photographic element according to claim 6 wherein said silver halide grains contain a metal dopant, which grains when coated on a photographic support, exposed to a light intensity scale, and developed for 5 minutes at 25° C. in test surface developer provide (a) a density of less than 0.25 and (b) a density of at least 5 times greater when this testing procedure is repeated modifying the test surface developer by the inclusion of 0.5 gram per liter of potassium iodide, the test surface developer being of the following composition:

| Water | 500.0 cc |
|---|---|
| N-methyl-p-aminophenol sulfate | 2.5 g |
| Sodium sulfite, desiccated | 30.0 g |
| Hydroquinone | 2.5 g |
| Sodium metaborate | 10.0 g |
| Potassium bromide | 0.5 g |
| Water to make | 1.0 liter. |

9. A process of obtaining a direct-positive image comprising imagewise exposing a photographic element comprised of a support and coated on the support, a silver halide emulsion layer comprising silver halide grains capable of forming an internal latent image and, adsorbed to the surface of the silver halide grains, a nucleating amount of a 3,3-disubstituted acylhydrazinophenylthiourea of the formula $$\underset{R-C-N-N-R^1-N-C-N}{\overset{O\phantom{xx}H\phantom{xx}H\phantom{xxxx}H\phantom{xx}S}{\overset{\|\phantom{xxxxxxxxxxxxxx}\|}{\phantom{x}}}}\overset{R^2}{\underset{R^3}{<}}$$

wherein

R is hydrogen or an alkyl, cycloalkyl, haloalkyl, alkoxyalkyl, or phenylalkyl substituent, $R^1$ is a phenylene or alkyl, halo-, or alkoxysubstituted phenylene group, and $R^2$ and $R^3$ are independently selected from among alkyl, haloalkyl, alkoxyalkyl, or phenylalkyl substituents having from 1 to 18 carbon atoms, a cycloalkyl substituent; a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur, and selenium atoms, the alkyl moieties, except as otherwise noted, in each instance include from 1 to 6 carbon atoms and the cycloalkyl moieties have from 3 to 10 carbon atoms, and selectively surface developing the silver halide grains remaining unexposed.

10. In an image transfer film unit which comprises a photographic element comprising a support bearing at least one silver halide emulsion layer containing radiation-sensitive internal latent image-forming silver halide grains and, adsorbed to the surface of said silver halide grains, a nucleating agent, said photographic element including an image dye-providing material within or in contact with said silver halide emulsion layer, an image-receiving means positioned to receive image dye from said photographic element, an alkaline processing composition, means containing and adapted to release said alkaline processing composition for contact with said emulsion layer, and a silver halide developing agent located in at least one of the photographic element and the alkaline processing composition, the improvement wherein said nucleating agent is a 3,3-disubstituted acylhydrazinophenylthiourea of the formula $$\underset{R-C-N-N-R^1-N-C-N}{\overset{O\phantom{xx}H\phantom{xx}H\phantom{xxxx}H\phantom{xx}S}{\overset{\|\phantom{xxxxxxxxxxxxxx}\|}{\phantom{x}}}}\overset{R^2}{\underset{R^3}{<}}$$

wherein

R is hydrogen or an alkyl, cycloalkyl, haloalkyl, alkoxyalkyl, or phenylalkyl substituent, $R^1$ is a phenylene or alkyl, halo-, or alkoxysubstituted phenylene group, and $R^2$ and $R^3$ are independently selected from among alkyl, haloalkyl, alkoxyalkyl, or phenylalkyl substituents having from 1 to 18 carbon atoms, a cycloalkyl substituent, a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur, and selenium atoms, the alkyl moieties, except as otherwise noted, in each instance include from 1 to 6 carbon atoms and the cycloalkyl moieties have from 3 to 10 carbon atoms.

11. An improved image transfer film unit according to claim 10 wherein said film unit incorporates an antifoggant.

12. An improved image transfer film unit according to claim 11 wherein said antifoggant is a benzotriazole antifoggant.

13. An improved image transfer film unit according to claim 10 wherein said 3,3-disubstituted acylhydrazinophenylthiourea is of the formula $$\underset{R-C-N-N\phantom{xxx}N-C-N}{\overset{O\phantom{xx}H\phantom{xx}H\phantom{xxxxxxxx}H\phantom{xx}S}{\overset{\|\phantom{xxxxxxxxxxxxxxxxxx}\|}{\phantom{x}}}}\overset{R^2}{\underset{R^3}{<}}$$

wherein

R is hydrogen or methyl and $R^2$ and $R^3$ are independently selected from among alkyl and phenylalkyl substituents, wherein the alkyl moieties are in each instance from 1 to 6 carbon atoms, and a phenyl nucleus having a Hammett sigma value-derived electron-withdrawing characteristic less positive than +0.50, or $R^2$ and $R^3$ together form a saturated heterocyclic nucleus forming a 5- or 6-membered ring, wherein the ring atoms are chosen from the class consisting of nitrogen, carbon, oxygen, sulfur, and selenium atoms.

14. An image transfer film unit comprising
(a) a photographic element comprising a support bearing
(1) a layer containing a blue-sensitive silver halide emulsion having in contact therewith an immobile material capable of releasing a mobile yellow image dye,
(2) a layer containing a green-sensitized silver halide emulsion having in contact therewith an immobile material capable of releasing a mobile magenta image dye, and
(3) a layer containing a red-sensitized silver halide emulsion having in contact therewith an immobile material capable of releasing a mobile cyan image dye, wherein each of said silver halide emulsions comprises silver halide grains having metal dopants occluded therein, which grains when coated on a photographic support, exposed to a light intensity scale, and developed for 5 minutes at 25° C. in test surface developer provide (a) a density of less than 0.4 and (b) a density of at least 0.5 less than when this testing procedure is repeated modifying the test surface developer by the inclusion of 0.5 gram per liter of potassium iodide,
(b) an image-receiving means positioned to receive image dye from said photographic element,
(c) an aqueous alkaline processing composition,
(d) means containing and adapted to release said alkaline processing composition into contact with said silver halide emulsions,
(e) a silver halide surface developing agent located in said processing composition, and
(f) from 1 to 100 mg per mole of silver of a nucleating agent adsorbed to said silver halide grains within at least one of said silver halide emulsion layers, said nucleating agent having the formula

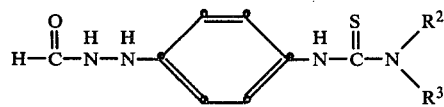

wherein
$R^2$ and $R^3$ are independently selected from among alkyl and phenylalkyl substituents, wherein the alkyl moieties are in each instance from 1 to 6 carbon atoms, and a phenyl nucleus having a Hammett sigma value-derived electron-withdrawing characteristic less positive than +0.50, or $R^2$ and $R^3$ together form a saturated heterocyclic nucleus forming a 5- or 6-membered ring, wherein the ring atoms are chosen from the class consisting of nitrogen, carbon, oxygen, sulfur, and selenium atoms, the test surface developer consisting essentially of

| Water (52° C.) | 500.0 cc |
|---|---|
| N-methyl-p-aminophenol sulfate | 2.5 g |
| Sodium sulfite, desiccated | 30.0 g |
| Hydroquinone | 2.5 g |
| Sodium metaborate | 10.0 g |
| Potassium bromide | 0.5 g |
| Water to make | 1 liter. |

15. A photographic element according to claim 14 wherein said silver halide grains contain a metal dopant, provide a maximum optical density less than 0.25 when coated on a support at a density of from 3 to 4 grams per square meter, exposed to a light intensity scale for a fixed time of from $1 \times 10^2$ to 1 second and developed for 5 minutes at 25° C. in the surface developer, and provide a maximum optical density at least 5 times greater than the above maximum density when the above procedure is repeated additionally including in the surface developer 0.5 gram per liter of potassium iodide to form an internal developer.

16. A photographic element according to claim 14 wherein the immobile materials capable of releasing mobile image dye are redox dye-releasers.

17. In a process of producing a visible image in an imagewise exposed photographic element having a support and, coated on the support, a silver halide emulsion layer comprising silver halide grains capable of forming an internal latent image and, adsorbed to the surface of the silver halide grains, a nucleating agent in an amount sufficient to promote development of unexposed silver halide grains comprising processing in an aqueous alkaline surface developer,
the improvement comprising
developing in the presence of a 3,3-disubstituted acylhydrazinophenylthiourea of the formula

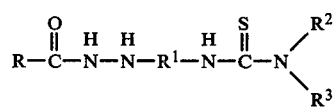

wherein
R is hydrogen or an alkyl, cycloalkyl, haloalkyl, alkoxyalkyl, or phenylalkyl substituent,
$R^1$ is a phenylene or alkyl, halo-, or alkoxysubstituted phenylene group, and
$R^2$ and $R^3$ are independently selected from among alkyl, haloalkyl, alkoxyalkyl, or phenylalkyl substituents having from 1 to 18 carbon atoms, a cycloalkyl substituent, a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur, and selenium atoms,
the alkyl moieties, except as otherwise noted, in each instance include from 1 to 6 carbon atoms and the cycloalkyl moieties have from 3 to 10 carbon atoms.

18. In a process according to claim 17 the further improvement in which the surface developer is at a pH in the range of from 13.9 to 11.8.

19. In a process according to claim 17 the further improvement in which the surface developer is at a pH in the range of from 12.0 to 13.0.

20. In a process of producing by surface development a visible image in an imagewise exposed photographic element having a support and, coated on the support, a silver halide emulsion layer comprising silver halide grains and a nucleating agent in an amount sufficient to promote surface development of unexposed silver halide grains, the silver halide grains having metal dopants occluded therein and which grains when coated on a photographic support, exposed to a light intensity scale, and developed for 5 minutes at 25° C. in test surface developer provide (a) a density of less than 0.4 and (b) a density of at least 0.5 less than when this testing procedure is repeated modifying the test surface developer by the inclusion of 0.5 gram per liter of potassium iodide, the test surface developer being of the following composition:

| Water | 500.0 cc |
|---|---|
| N-methyl-p-aminophenol sulfate | 2.5 g |
| Sodium sulfite, desiccated | 30.0 g |
| Hydroquinone | 2.5 g |
| Sodium metaborate | 10.0 g |
| Potassium bromide | 0.5 g |
| Water to make | 1.0 liter, | the improvement wherein
the nucleating agent is a 3,3-disubstituted acylhydrazinophenylthiourea of the formula

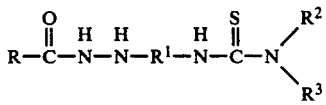

wherein
r is hydrogen or an alkyl, cycloalkyl, haloalkyl, alkoxyalkyl, or phenylalkyl substituent,
$R^1$ is a phenylene or alkyl, halo-, or alkoxysubstituted phenylene group, and
$R^2$ and $R^3$ are independently selected from among alkyl, haloalkyl, alkoxyalkyl, or phenylalkyl substituents having from 1 to 18 carbon atoms, a cycloalkyl substituent, a phenyl nucleus having a Hammett sigma value-derived electron-withdrawing characteristic less positive than +0.50, and naphthyl, or $R^2$ and $R^3$ together form a heterocyclic nucleus forming a 5- or 6-membered ring, wherein the ring atoms are chosen from the class consisting of nitrogen, carbon, oxygen, sulfur and selenium atoms.

the alkyl moieties, except as otherwise noted, in each instance include from 1 to 6 carbon atoms and the cycloalkyl moieties have from 3 to 10 carbon atoms, and surface development occurring at a pH in the range of from 12.0 to 13.0.

21. In a process according to claim 20 the further improvement in which the nucleating agent is of the formula

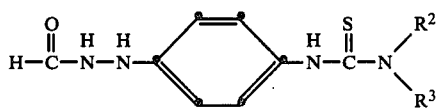

wherein
$R^2$ and $R^3$ are independently selected from among alkyl and phenylalkyl substituents, wherein the alkyl moieties are in each instance from 1 to 6 carbon atoms, and a phenyl nucleus having a Hammett sigma value-derived electron-withdrawing characteristic less positive than +0.50, or $R^2$ and $R^3$ together form a saturated heterocyclic nucleus forming a 5- or 6-membered ring, wherein the ring atoms are chosen from the class consisting of nitrogen, carbon, oxygen, sulfur, and selenium atoms.

22. In a process according to claim 20 the further improvement wherein a visible image is transferred to a receiver.

23. In a process according to claim 22 the further improvement wherein the photographic element is a dye image transfer photographic element containing in contact with the silver halide emulsion layer an initially immobile dye releasing material and image dye is transferred to the receiver to form a visible image.

* * * * *